US007492911B2

(12) United States Patent
Nakajima et al.

(10) Patent No.: US 7,492,911 B2
(45) Date of Patent: Feb. 17, 2009

(54) NOISE REDUCING DEVICE

(75) Inventors: Tatsumi Nakajima, Inzai (JP); Kazunori Suzuki, Inzai (JP)

(73) Assignee: Takenaka Corporation, Osaka-Shi (JP)

( * ) Notice: Subject to any disclaimer, the term of this patent is extended or adjusted under 35 U.S.C. 154(b) by 808 days.

(21) Appl. No.: 10/846,419

(22) Filed: May 14, 2004

(65) Prior Publication Data

US 2005/0157890 A1 Jul. 21, 2005

(30) Foreign Application Priority Data

May 15, 2003 (JP) ............................ 2003-136698
May 12, 2004 (JP) ............................ 2004-142102

(51) Int. Cl.
*H04R 3/02* (2006.01)
*H04R 3/00* (2006.01)
*H04B 15/00* (2006.01)
*A61F 11/06* (2006.01)

(52) U.S. Cl. .................... 381/73.1; 381/94.1; 381/71.1; 381/71.2; 381/71.4; 381/122; 381/92

(58) Field of Classification Search ................ 381/73.1, 381/71.1–71.2, 92, 122, 94.1, 71.4
See application file for complete search history.

(56) References Cited

U.S. PATENT DOCUMENTS

2002/0048376 A1 * 4/2002 Ukita .......................... 381/92

FOREIGN PATENT DOCUMENTS

| | | | |
|---|---|---|---|
| GB | 2 257 327 A | 1/1993 | |
| JP | 02-094999 | 4/1990 | |
| JP | 03-284098 | 12/1991 | |
| JP | 04-303898 | 10/1992 | |
| JP | 04-308899 | 10/1992 | |
| JP | 06-059687 | 3/1994 | |
| JP | 07-020880 | 1/1995 | |
| JP | 07-074590 | 3/1995 | |
| JP | 07-104771 | 4/1995 | |
| JP | 07-234689 | 9/1995 | |
| JP | 07-261774 | 10/1995 | |
| JP | 08-033092 | 2/1996 | |
| JP | 08-083080 | 3/1996 | |
| JP | 08-179782 | 7/1996 | |
| JP | 09-054593 | 2/1997 | |
| JP | 10-011073 | 1/1998 | |
| JP | 2001-142468 | 5/2001 | |
| JP | 2001-172925 | 6/2001 | |
| JP | 2003-108151 | 4/2003 | |

OTHER PUBLICATIONS

Anon., "Electronic Sound Insulation Wall for Reducing Noise by Half," *Nikkei Business*, pp. 82-84, Oct. 7, 2002.
Berakek, L., *Acoustics*, pp. 93-97, The McGraw-Hill Co.: New York, NY (1954).
Kuttruff, H., *Room Acoustics*, pp. 10-14, Applied Science Publishers Ltd: London, GB (1979).

* cited by examiner

*Primary Examiner*—Vivian Chin
*Assistant Examiner*—George C Monikang
(74) *Attorney, Agent, or Firm*—Dorsey & Whitney LLP

(57) ABSTRACT

The present invention provides an active control type noise reducing device that is disposed at a sound barrier and with which can be obtained an excellent noise reduction effect with respect to moving sound sources. Linear array of flat loudspeakers are arranged in ascending order from an incoming side of automobiles towards an outgoing side. Delay times of 0, τ, 2τ, . . . , 8τ are respectively given in the arrangement order to the linear array of flat loudspeakers. By delaying signals in correspondence to the arrangement order, the wavefront of a control sound can be slanted in a diagonal direction. Namely, "line sound sources", where sound sources are linearly arranged, arc pseudo-realized.

6 Claims, 21 Drawing Sheets

NOISE REDUCING DEVICE

CROSS-REFERENCE TO RELATED APPLICATIONS

This application claims priority under 35 USC 119 from Japanese Patent Application No. 2003-136698, the disclosure of which is incorporated by reference herein.

BACKGROUND OF THE INVENTION

1. Field of the Invention

The present invention relates to a noise reducing device, and in particular to an active control type noise reducing device that is added to a sound barrier and reduces noise by active control.

2. Description of the Related Art

In Japan, roadways pass through residential areas and alongside hospitals that are supposed to be quiet, and large trucks come and go through these roadways day and night. Motorcycles of motorcycle gangs also travel on these roadways spreading loud explosive noise. The problem of road traffic noise is becoming manifest not only in urban areas but also in rural areas and has become a large social problem.

In recent years, a system called active noise control (ANC) that reduces noise by active control has gathered attention. The noise cancellation principle of ANC is "superposing antiphase sound waves on the original sound waves that are to be canceled". Namely, as shown in FIG. 1, active noise control reduces the sound pressure level by superposing, on noise A emitted by a noise source, a control sound B emitted from a control sound source.

This noise cancellation principle can be applied to, for example, diffracted noise that is emitted from a noise source, diffracted at the top of a sound bind travels beyond the barrier. As shown in FIG. 2, noise 12 emitted from a noise source S receives the action of diffraction as a wave phenomenon when the noise 12 passes through the vicinity of the top (control point C) of a sound barrier 10. This means that the control point C becomes a new sound source (secondary sound source) with this point at the center. With respect to the control point C, a control sound 16 is emitted from a control sound source (speaker) 14 disposed in the vicinity of the sound barrier 10. In this case, the control sound 16 is produced so that, at the control point C, the noise 12 from the noise source S and the control sound 16 from the control speaker 14 have opposite phases at the same amplitude. Thus, when the noise is observed at an observation point O located in a region at the side of the sound barrier 10 opposite from that of the noise source S, a noise reducing effect equal to or greater than the amount of noise reduced by the sound barrier 10 can be obtained.

Road traffic noise is noise generated by continuously traveling, plural moving sound sources (automobiles). The main noises generated by automobiles traveling on expressways are engine sounds and tire running sounds. These noises are diffracted at the tops of sound barriers along the expressways and are propagated to the expressway environs.

Conventionally, as technology that reduces road traffic noise by ANC, active soft edge sound barriers (ASE sound barriers) have been proposed and utilized (e.g., see the Oct. 7, 2002 issue of *Nikkei Business; Acoustical Science and Technology* (Acoustic Society of Japan), Vol. 58, No. 12 (2002), pp. 753-760; and Japanese Patent Application Laid-Open Publication (JP-A) Nos. 9-119114, 2001-172925 and 2002-6854). ASE sound barriers form an acoustically soft (complex acoustic reflectivity is −1) boundary at the end (edge) of a sound barrier by ANC, to thereby reduce low-frequency noise of 500 Hz or less mainly diffracted at the top of the sound barrier. The noise cancellation principle here is one where sound is reduced by making the noise impedance Z at the boundary of the top portion of the sound barrier equal to ρc, i.e., the same as the acoustic impedance of the air to completely absorb the sound.

However, an ASE sound barrier only exhibits a noise reducing effect in the vicinity of the upper surface of an ASH cell that is the acoustic controller. Thus, there is the problem that, when an ASE sound barrier is used to try to reduce road traffic noise, numerous ASE cells must be disposed along the sound barrier with no space therebetween, and the device becomes large. Also, the noise reducing effect of an ASE sound barrier is at most about 4 dB, which is hardly a sufficient noise reducing effect.

SUMMARY OF THE INVENTION

The present invention has been devised in light of the above-described circumstances, and it is an object therefore to provide an active control type noise reducing device that is added to a sound barrier and has an excellent noise reduction effect with respect to moving sound sources.

In order to achieve this object, a first noise reducing device of the invention comprises: a first microphone disposed at a control point set at an outer side of a sound barrier that reduces noise emitted from a noise source; a second microphone disposed at an inner side of the sound barrier and including a directivity in a predetermined direction so as to pick up the noise that is emitted from the noise source and made incident from a diagonal direction with respect to the sound barrier; computing means that computes, on the basis of the output of the first microphone and the output of the second microphone, a filter factor with an explicit method so that the noise at the control point is reduced; a filter that outputs a control signal digitally filtered on the basis of the filter factor computed by the computing means and the output of the second microphone; a control sound source in which unidirectional linear array of plural loudspeakers are arranged in a predetermined direction and which is disposed so that a control sound configured by sound emitted from the linear array of plural loudspeakers is diffracted at an upper edge of the sound barrier and reaches the control point; and an input circuit that inputs, to the linear array of plural loudspeakers and in correspondence to the arrangement order of the linear array of plural loudspeakers, the control signal and a delay control signal in which the control signal is delayed by predetermined times in correspondence to the direction in which the noise is made incident at the sound barrier.

In the first noise reducing device of the invention, the sound barrier that reduces the noise emitted from the noise source is disposed. The control point for controlling the noise is set at the outer side of the sound barrier, and the first microphone is disposed at this control point. Additionally, the second microphone (sound source microphone) is disposed at the inner side of the sound barrier and includes a directivity in a predetermined direction so as to pick up the noise that is emitted from the noise source and made incident from a diagonal direction with respect to the sound barrier.

The computing means computes, on the basis of the output of the first microphone and the output of the second microphone, a filter factor with an explicit method so that the noise at the control point is reduced. The filter factor computed by the computing means is set in the filter. The filter whose filter factor is set conducts digital filtering using the digital value of the output of the second microphone and the set filter factor, and outputs the control signal.

The first noise reducing device of the invention is also disposed with the control sound source in which unidirectional linear array of plural loudspeakers are arranged in a predetermined direction and which is disposed so that a control sound configured by sound emitted from the linear array of plural loudspeakers is diffracted at an upper edge of the sound barrier and reaches the control point. The input circuit inputs, to the linear array of plural loudspeakers of the control sound source and in correspondence to the arrangement order of the linear array of plural loudspeakers, the control signal and a delay control signal in which the control signal is delayed by predetermined times in correspondence to the direction in which the noise is made incident at the sound barrier.

In this manner, by delaying the linear array of loudspeakers arranged in the control sound source in correspondence to the incident direction of the noise, the control sound can be emitted in the same direction as the incident direction of the noise, and the noise made incident at the sound barrier from a predetermined direction can be effectively reduced. Namely, an excellent noise reduction effect with respect to moving sound sources can be obtained. Also, because the control sound is diffracted at the upper edge of the sound barrier and reaches the control point, the noise emitted from the noise source is controlled by the diffracted control sound at the control point, and a larger noise reduction effect can be obtained. Moreover, by computing the filter factor with the explicit method, a window can be multiplied by the impulse response measured during the computation process, whereby stable control can be conducted without being affected by disturbances.

In the first noise reducing device, the control sound source may be plurally disposed. In this case, the input circuit inputs, per control sound source and in correspondence to the arrangement order of the linear array of plural loudspeakers, the control signal and the delay control signal in which the control signal is delayed by predetermined times in correspondence to the direction in which the noise is made incident at the sound barrier. Thus, noise made incident at the sound barrier from different directions can be effectively reduced.

In order to achieve the aforementioned object, a second noise reducing device of the invention comprises: a first microphone disposed at a control point set at an outer side of a sound barrier that reduces noise emitted from a noise source; a second microphone disposed at an inner side of the sound barrier and including a directivity in a predetermined direction so as to pick up the noise that is emitted from the noise source and made incident from a diagonal direction with respect to the sound barrier; a third microphone disposed at an inner side of the sound barrier and including a directivity in a predetermined direction so as to pick up the noise that is emitted from the noise source and made incident from a front direction with respect to the sound barrier; computing means that computes, on the basis of the output of the first microphone and the output of the second microphone, a first filter factor with an explicit method so that the noise at the control point is reduced, and which computes, on the basis of the output of the first microphone and the output of the third microphone, a second filter factor with an explicit method so that the noise at the control point is reduced; a first filter that outputs a first control signal digitally filtered on the basis of the filter factors computed by the computing means and the output of the second microphone; a second filter that generates a second control signal digitally filtered on the basis of the second filter factor computed by the computing means and the output of the third microphone; a control sound source in which unidirectional linear array of plural loudspeakers are arranged in a predetermined direction and which is disposed so that a control sound configured by sound emitted from the linear array of plural loudspeakers is diffracted at an upper edge of the sound barrier and reaches the control point; and an input circuit that inputs, to the linear array of plural loudspeakers and in correspondence to the arrangement order of the linear array of plural loudspeakers, the first control signal and a first delay control signal in which the first control signal is delayed by predetermined times in correspondence to the direction in which the noise is made incident at the sound barrier, and which inputs the second control signal to the linear array of plural loudspeakers.

In the second noise reducing device of the invention, in addition to the second microphone that picks up the noise made incident with respect to the sound barrier from a diagonal direction, the third microphone that picks up the noise made incident with respect to the sound barrier from the front direction is disposed. The first filter outputs the first control signal digitally filtered on the basis of the filter factors computed by the computing means and the output of the second microphone, and the second filter outputs the second control signal digitally filtered on the basis of the second filter factor computed by the computing means and the output of the third microphone.

By respecting disposing, in correspondence to the control sound source, the second microphone that picks up the noise made incident with respect to the sound barrier from a diagonal direction and the first filter corresponding to this, and also the third microphone that picks up the noise made incident with respect to the sound barrier from the front direction and the second filter corresponding to this, the noises made incident from different directions can be respectively detected and independently controlled.

Also, the input circuit inputs, to the linear array of plural loudspeakers and in correspondence to the arrangement order of the linear array of plural loudspeakers, the first control signal and a first delay control signal in which the first control signal is delayed by predetermined times in correspondence to the direction in which the noise is made incident at the sound barrier, and which inputs the second control signal to the linear array of plural loudspeakers. In this manner, even in a case where there are at least two incident directions of the noise, by delaying the linear array of loudspeakers arranged in the control sound source in correspondence to the incident directions of the noise, the control sound can be emitted in the same directions as the incident directions of the noise, and the noise made incident at the sound barrier from predetermined directions can be effectively reduced.

In the second noise reducing device, the control sound source may be plurally disposed. In this case, the input circuit inputs, in correspondence to the arrangement order of the linear array of plural loudspeakers, the first control signal and the first delay control signal to the linear array of plural loudspeakers configuring a predetermined control sound source, and which inputs the second control signal to the linear array of plural loudspeakers configuring another control sound source.

In order to achieve the aforementioned object, a third noise reducing device of the invention comprises: a first microphone disposed at a control point set at an outer side of a sound barrier that reduces noise emitted from a noise source; a second microphone disposed at an inner side of the sound barrier and including a directivity in a predetermined direction so as to pick up the noise that is emitted from the noise source and made incident from a first diagonal direction with respect to the sound barrier; a third microphone disposed at an inner side of the sound barrier and including a directivity in a predetermined direction so as to pick up the noise that is emitted from the noise source and made incident from a front direction with respect to the sound barrier; a fourth microphone disposed at an inner side of the sound barrier and including a directivity in a predetermined direction so as to pick up the noise that is emitted from the noise source and made incident at the sound barrier from a second diagonal direction that is different from the first diagonal direction; computing means that computes, on the basis of the output of the first microphone and the output of the second microphone, a first filter factor with an explicit method so that the noise at the control point is reduced, and which computes, on the basis of the output of the first microphone and the output of the third microphone, a second filter factor with an explicit method so that the noise at the control point is reduced, and which computes, on the basis of the output of the first microphone and the output of the fourth microphone, a third filter factor with an explicit method so that the noise at the control point is reduced; a first filter that outputs a first control signal digitally filtered on the basis of the filter factors computed by the computing means and the output of the second microphone; a second filter that generates a second control signal digitally filtered on the basis of the second filter factor computed by the computing means and the output of the third microphone; a third filter that generates a third control signal digitally filtered on the basis of the third filter factor computed by the computing means and the output of the fourth microphone; a control sound source in which plural unidirectional linear array of loudspeakers are arranged in a predetermined direction and which is disposed so that a control sound configured by sound emitted from the linear array of plural loudspeakers is diffracted at an upper edge of the sound barrier and reaches the control point; and an input circuit that inputs, to the linear array of plural loudspeakers and in correspondence to the arrangement order of the linear array of plural loudspeakers, the first control signal and a first delay control signal in which the first control signal is delayed by predetermined times in correspondence to the direction in which the noise is made incident at the sound barrier and the third control signal and a second delay control signal in which the third control signal is delayed by predetermined times in correspondence to the direction in which the noise is made incident at the sound barrier, and which inputs the second control signal to the linear array of plural loudspeakers.

In the third noise reducing device of the invention, in addition to the second microphone that picks up the noise made incident with respect to the sound barrier from the first diagonal direction, the third microphone that picks up the noise made incident from the front direction with respect to the sound barrier and the fourth microphone that picks up the noise made from the second diagonal direction that is different from the first diagonal direction are disposed. The first filter outputs the first control signal digitally filtered on the basis of the first filter factor computed by the computing means and the output of the second microphone, the second filter outputs the second control signal digitally filtered on the basis of the second filter factor computed by the computing means and the output of the third microphone, and the third DSP control circuit outputs the third control signal digitally filtered on the basis of the third filter factor computed by the computing means and the output of the fourth microphone.

By respectively disposing, in correspondence to the control sound source, the second microphone that picks up the noise made incident with respect to the sound barrier from the first diagonal direction and the first filter corresponding to this, the third microphone that picks up the noise made incident with respect to the sound barrier from the front direction and the second filter corresponding to this, and the fourth microphone that picks up the noise made incident with respect to the sound barrier from the second diagonal direction and the third filter corresponding to this, the noises made incident from different directions can be respectively detected and independently controlled.

Additionally, the input circuit inputs, to the linear array of plural loudspeakers and in correspondence to the arrangement order of the linear array of plural loudspeakers, the first control signal and a first delay control signal in which the first control signal is delayed by predetermined times in correspondence to the direction in which the noise is made incident at the sound barrier, inputs the second control signal to the linear array of plural loudspeakers, and input the third control signal and a second delay control signal in which the third control signal is delayed by predetermined times in correspondence to the direction in which the noise is made incident at the sound barrier.

In this manner, even in a case where there are at least three incident directions of the noise, by delaying the linear array of loudspeakers arranged in the control sound source in correspondence to the incident directions of the noise, the control sound can be emitted in the same directions as the incident directions of the noise, and the noise made incident at the sound barrier from predetermined directions can be effectively reduced.

In the third noise reducing device, the control sound source may be plurally disposed. In this case, the input circuit inputs, to the linear array of plural loudspeakers configuring a predetermined control sound source and in correspondence to the arrangement order of the linear array of plural loudspeakers, the first control signal and the first delay control signal delayed by time corresponding to the direction in which the noise is made incident at the sound barrier, and which inputs the second control signal to the linear array of plural loudspeakers configuring another control sound source, and which inputs, to the linear array of plural loudspeakers configuring yet another control sound source and in correspondence to the arrangement order of the linear array of plural loudspeakers, the third control signal and the second delay control signal delayed by times corresponding to the direction in which the noise is made incident at the sound barrier.

As described above, according to the invention, in an active control type noise reducing device added to a sound barrier, a control sound can be emitted in the same direction as the incident direction of noise, and noise made incident at the sound barrier from a predetermined direction can be effectively reduced. Namely, there is the effect that an excellent noise reduction effect with respect to moving sound sources can be obtained.

Also, because the control sound is diffracted at the upper edge of the sound barrier and reaches the control point, there is the effect that the noise emitted from the noise source is controlled by the diffracted control sound at the control point, and a larger noise reduction effect can be obtained.

DETAILED DESCRIPTION OF THE INVENTION

Embodiments where a noise reducing device of the invention is applied to a traffic noise reducing system on an expressway will be described in detail below with reference to the drawings.

FIRST EMBODIMENT (Noise Reduction Control Zone)

Figure 1:
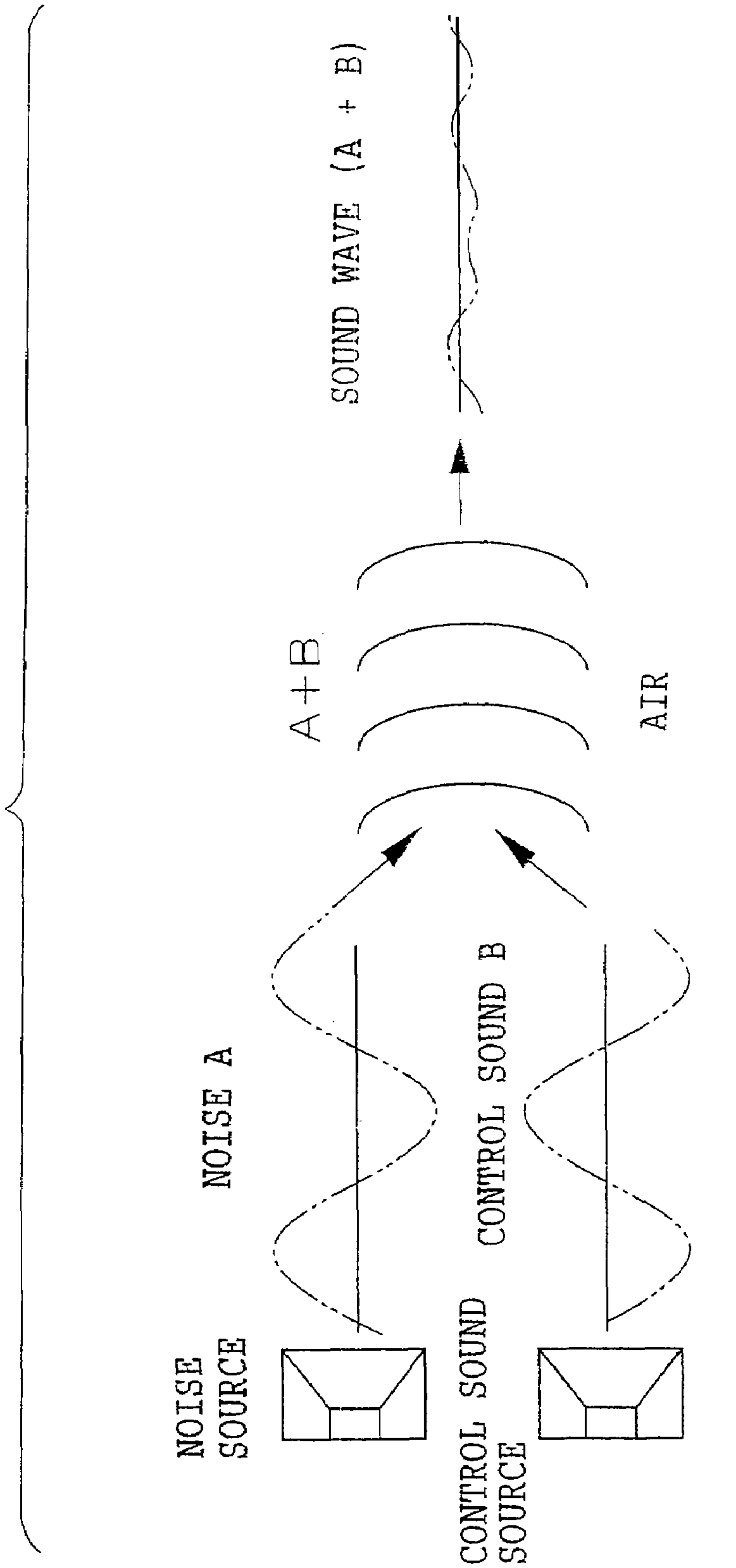
FIG. 1 (PRIOR ART)
FIG. 1 is a diagram for describing the noise cancellation principle of active noise control (ANC)
Figure 2:
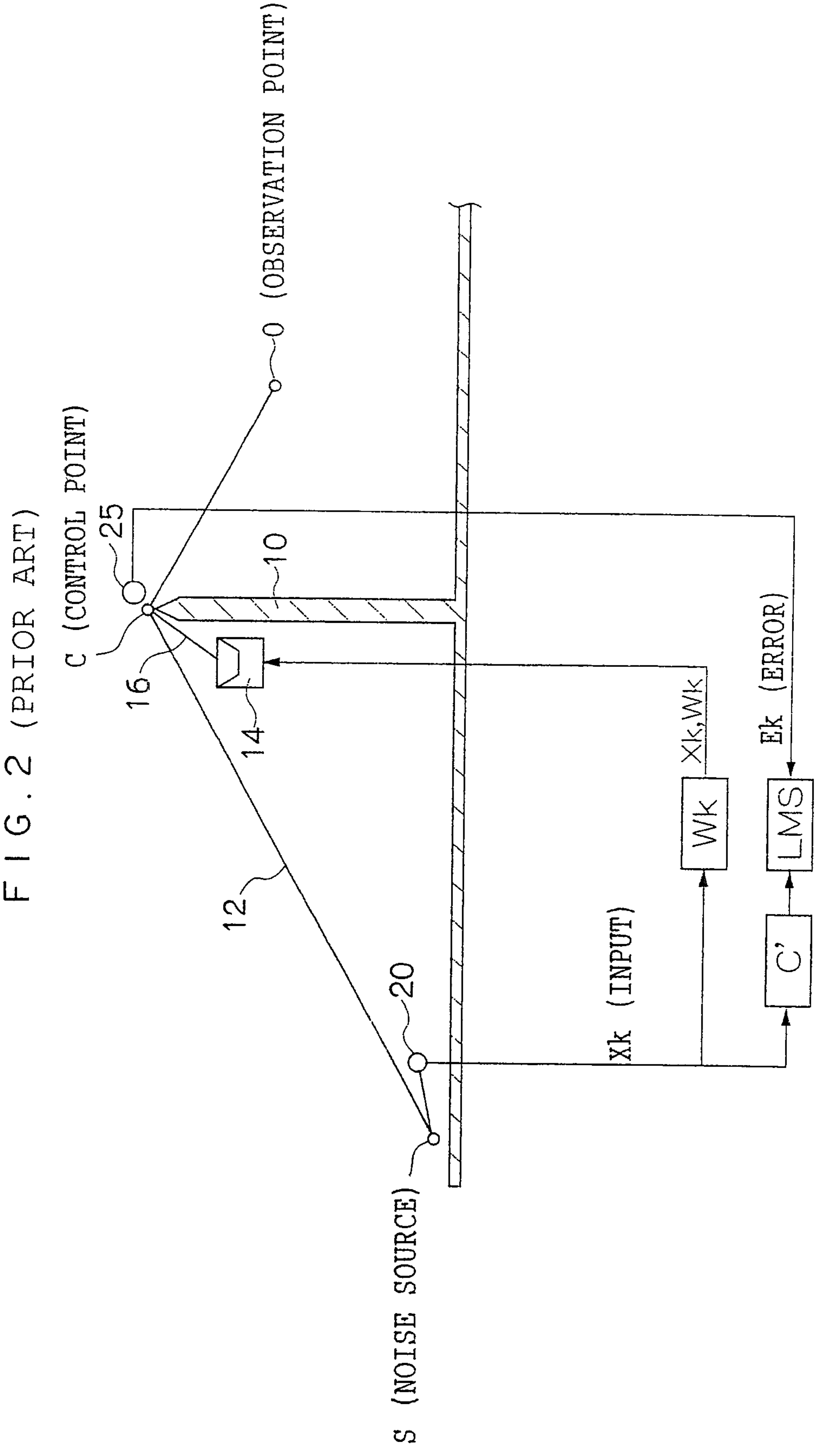
FIG. 2 (PRIOR ART)
FIG. 2 is a schematic diagram showing the configuration of a sound barrier disposed with a conventional ANC system.
Figure 3A:
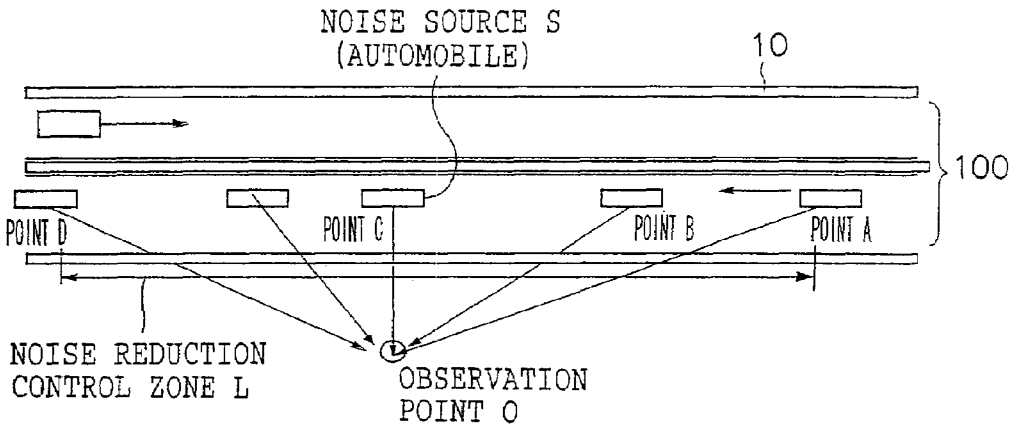
FIG. 3A is a diagram showing the positional relation of automobiles (noise sources S) traveling on an expressway, a noise observation point O and a noise reduction control zone L.

In the present embodiment, as shown in FIG. 3A, sound barriers 10 of a predetermined height are disposed at both sides of an expressway 100 parallel to the road in order to reduce noise emitted from an automobile that is a noise source S. The sound barriers 10 are configured by metal panels such as iron panels that are disposed vertically with respect to the road surface. It should be noted that noise reducing reinforcement panels may also be disposed at the noise source S sides of the sound barriers 10. It is preferable for the noise reducing reinforcement panels themselves to have a bass noise reducing capability of at least 10 dB. For example, a panel where a noise absorbing material such as a glass wall is adhered to the panel surfaces at the noise source S sides can be appropriately used.

Figure 3B:
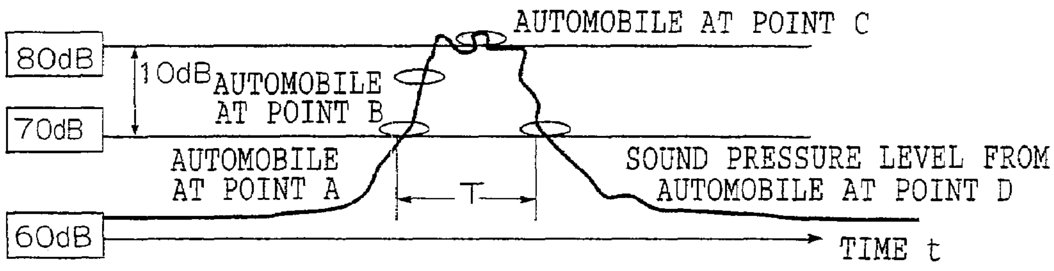
FIG. 3B is a graph showing the sound pressure level at the observation point O of noise propagated from the positions of the noise sources S.

When an observation point O is set at the outer side of the sound barriers 10, noise propagates from various directions to the observation point O when the automobile is traveling on the expressway 100, because the position of the noise source S changes from a point A to a point B, a point C and a point D in correspondence to the travel of the automobile. FIG. 3B shows the sound pressure level at the observation point O of the noise propagating from the respective positions of the sound source S. The sound pressure level from points A and D is 70 dB (decibels), and the sound pressure level from point C positioned in front of the observation point O is 80 dB. For example, assuming that V (km/h) represents the traveling velocity of the automobile and T (seconds) represents the time that a sound pressure level of at least 70 dB continues, a noise reduction control zone L (m) for controlling and reducing noise of at least 70 dB is expressed by the following equation.

$$L = \frac{1000}{3600} \times VT$$

(Noise Control Unit)

Figure 4:
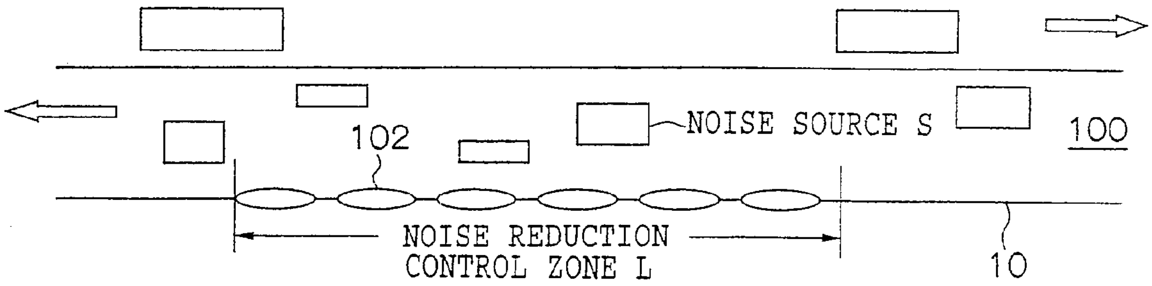
FIG. 4 is a plan diagram showing the disposition of a noise control unit in the control zone L.

As shown in FIG. 4, the control zone L is divided into plural small zones (six in the drawing) of a length of 1 to several meters, and a noise control unit 102 is disposed in each divided small zone.

Figure 5:
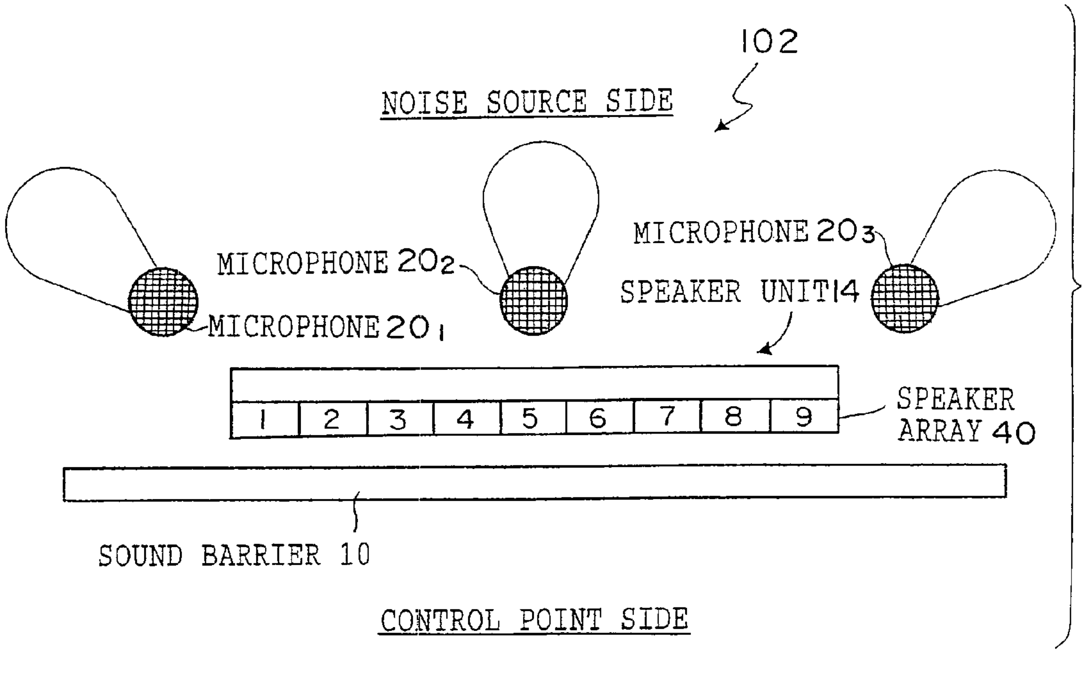
FIG. 5 is a plan diagram showing the schematic configuration of a noise control unit of a first embodiment of the present invention.

As shown in FIG. 5, each noise control unit 102 is disposed at the noise source side of the sound barrier 10 and includes a speaker unit 14, where plural (nine in the drawing) linear array of flat loudspeakers are arranged in one row along the sound barrier 10, and plural (three in the drawing) sound source microphones $\mathbf{20}_1$ to $\mathbf{20}_3$ disposed in the vicinity of the speaker unit 14. The sound source microphones $\mathbf{20}_1$ and $\mathbf{20}_3$ are respectively disposed at the incoming side and the outgoing side of the automobile, and the sound source microphone $\mathbf{20}_2$ is disposed in front of the sound barrier 10. Each of the sound source microphones $\mathbf{20}_1$ to $\mathbf{20}_3$ has a strong directivity in the incident direction (in the drawing, the two diagonal directions at the incoming side and the outgoing side and the front direction) of noise waves serving as the control target.

Figure 6:
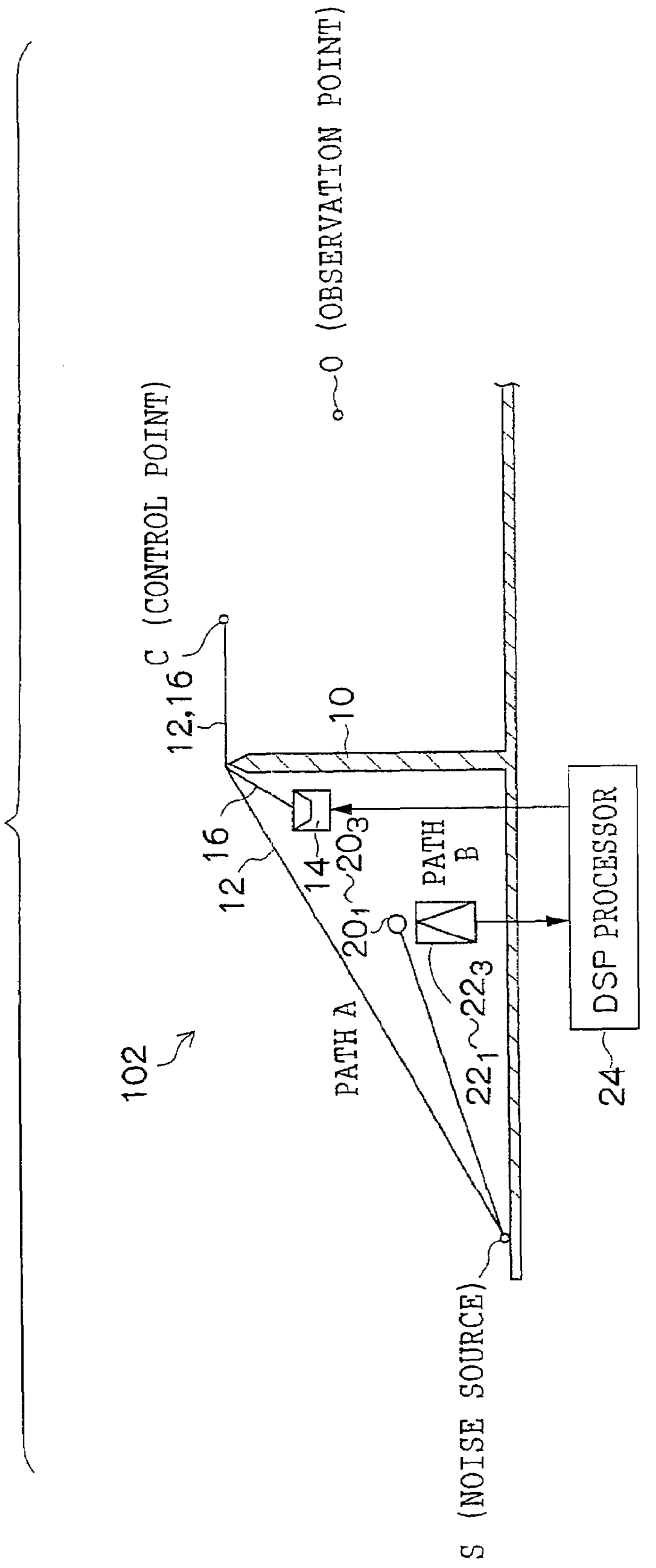
FIG. 6 is a schematic cross-sectional diagram where the noise control unit of the first embodiment of the present invention is cut at a plane perpendicular to a sound barrier.

As shown in FIG. 6, the speaker unit 14 is disposed at the inner side of the sound barrier 10 and at a predetermined distance away from the upper edge of the sound barrier 10, so that a control sound 16 is diffracted at the top of the sound barrier 10. The speaker unit 14 emits the control sound 16 towards the top of the sound barrier 10 so that the control sound 16 diffracted at the top of the sound barrier 10 reaches a control point C disposed at the outer side of the sound barrier 10 and in the vicinity of the speaker unit 14. By using diffracted sound in this manner to implement ANC, a larger effect can be obtained in order to reduce the noise that is emitted from the sound source S and diffracted at the top of the sound barrier 10. It should be noted that it is preferable for the length of the speaker unit 14 in the speaker arrangement direction to be the same as the distance between the top of the sound barrier and the control point C. For example, a length of 1 to several meters is preferable.

Each noise control unit 102 is disposed with a DSP processor 24 that conducts DSP (Digital Signal Processing). The DSP processor 24 is connected to each of the sound source microphones $\mathbf{20}_1$ to $\mathbf{20}_3$ via preamplifiers $\mathbf{22}_1$ to $\mathbf{22}_3$ and is also connected to the speaker unit 14. The sound waves picked up by each of the sound source microphones $\mathbf{20}_1$ to $\mathbf{20}_3$ are amplified by the corresponding preamplifiers $\mathbf{22}_1$ to $\mathbf{22}_3$ and inputted to the DSP processor 24.

Assuming that R1 (m) represents the distance along the propagation direction of the sound waves from the noise source S to the control point C, that R2 (m) represents a similar same distance from the speaker unit 14 to the control point C and that R3 (m) represents a similar distance from the noise source S to any of the sound source microphones $\mathbf{20}_1$ to $\mathbf{20}_3$, an arrival time T1 (ms) of the noise directly (path A) to the control point C and an arrival time T2 (ms) of the noise via the DSP processor 24 are expressed by the following equations assuming that $T_{DSP}$ represents the processing time by the DSP processor 24.

$$T1=R1/c$$

$$T2=(R2+R3)/c+T_{DSP}$$

Here, because R1>R2+R3, T1>T2. Also, because the DSP processor 24 requires about 1 ms of time for processing, the sound source microphones $\mathbf{20}_1$ to $\mathbf{20}_3$ are respectively disposed so that $T_{DSP}=1$, i.e., to satisfy the relation T2+1<T1. Further here, c represents sound velocity (m/sec).

Figure 7:
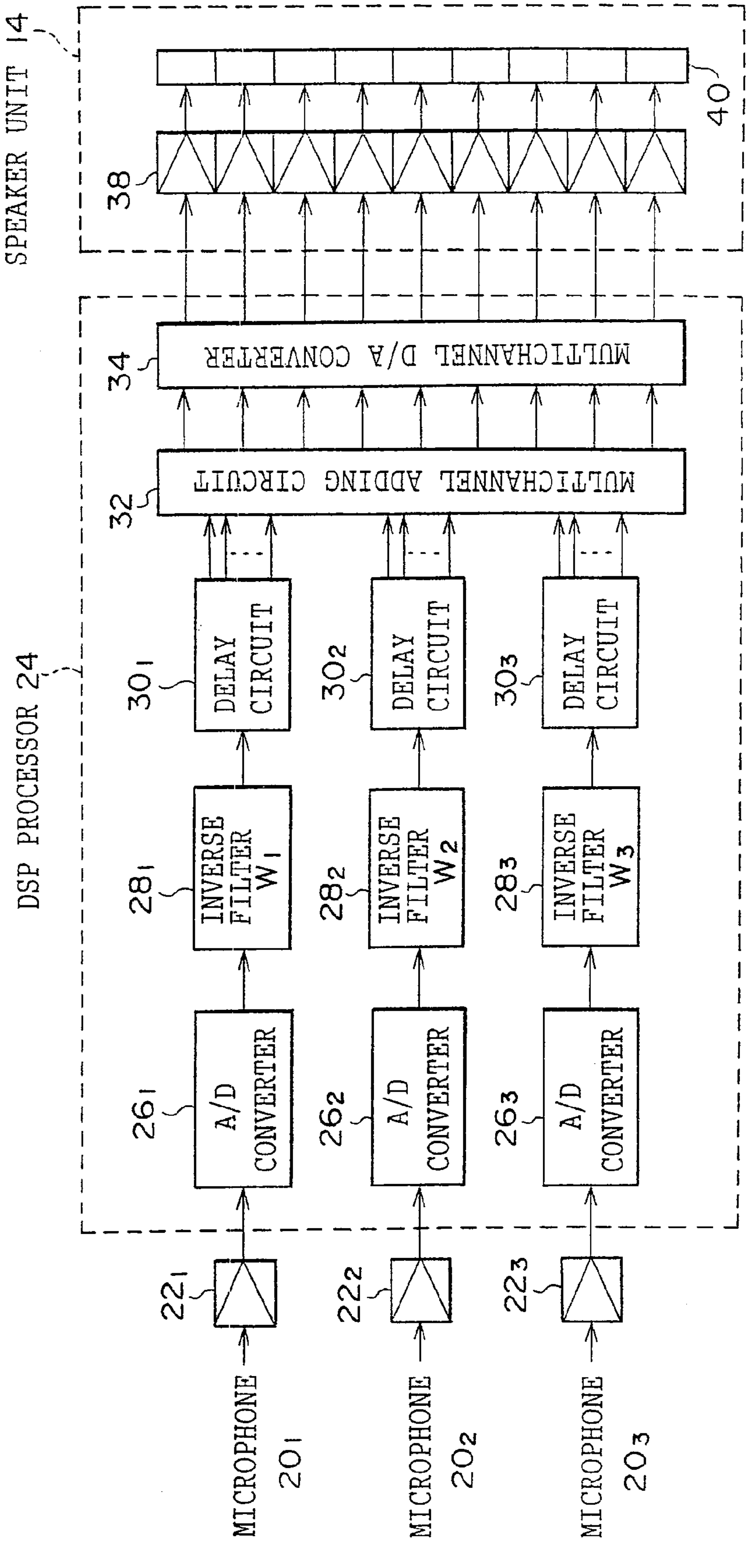
FIG. 7 is a block diagram showing the schematic configuration of the noise control unit of the first embodiment of the present invention.

As shown in FIG. 7, the DSP processor 24 includes A/D converters $\mathbf{26}_1$ to $\mathbf{26}_3$ that are disposed in correspondence to the preamplifiers $\mathbf{22}_1$ to $\mathbf{22}_3$ and convert analog signals to digital signals; time-invariant inverse filters $\mathbf{28}_1$ to $\mathbf{28}_3$ whose filter factors are predetermined; delays circuits $\mathbf{30}_1$ to $\mathbf{30}_3$ that delay signals in response to the arrangement order of the linear array of flat loudspeakers; a multichannel adding circuit 32; and a multichannel D/A converter 34 that converts digital signals to analog signals. It should be noted that the filter factors $W_1$, $W_2$ and $W_3$ are computed by a computer and set in the respective inverse filters $\mathbf{28}_1$ to $\mathbf{28}_3$. The method of computing the filter factors will be described later.

The inverse filters $\mathbf{28}_1$ to $\mathbf{28}_3$ use digital signals inputted from the A/D converters $\mathbf{26}_1$ to $\mathbf{26}_3$ and the set filter factors to conduct digital filtering. The filtered signals are inputted to the delay circuits $\mathbf{30}_1$ to $\mathbf{30}_3$.

Figure 8:
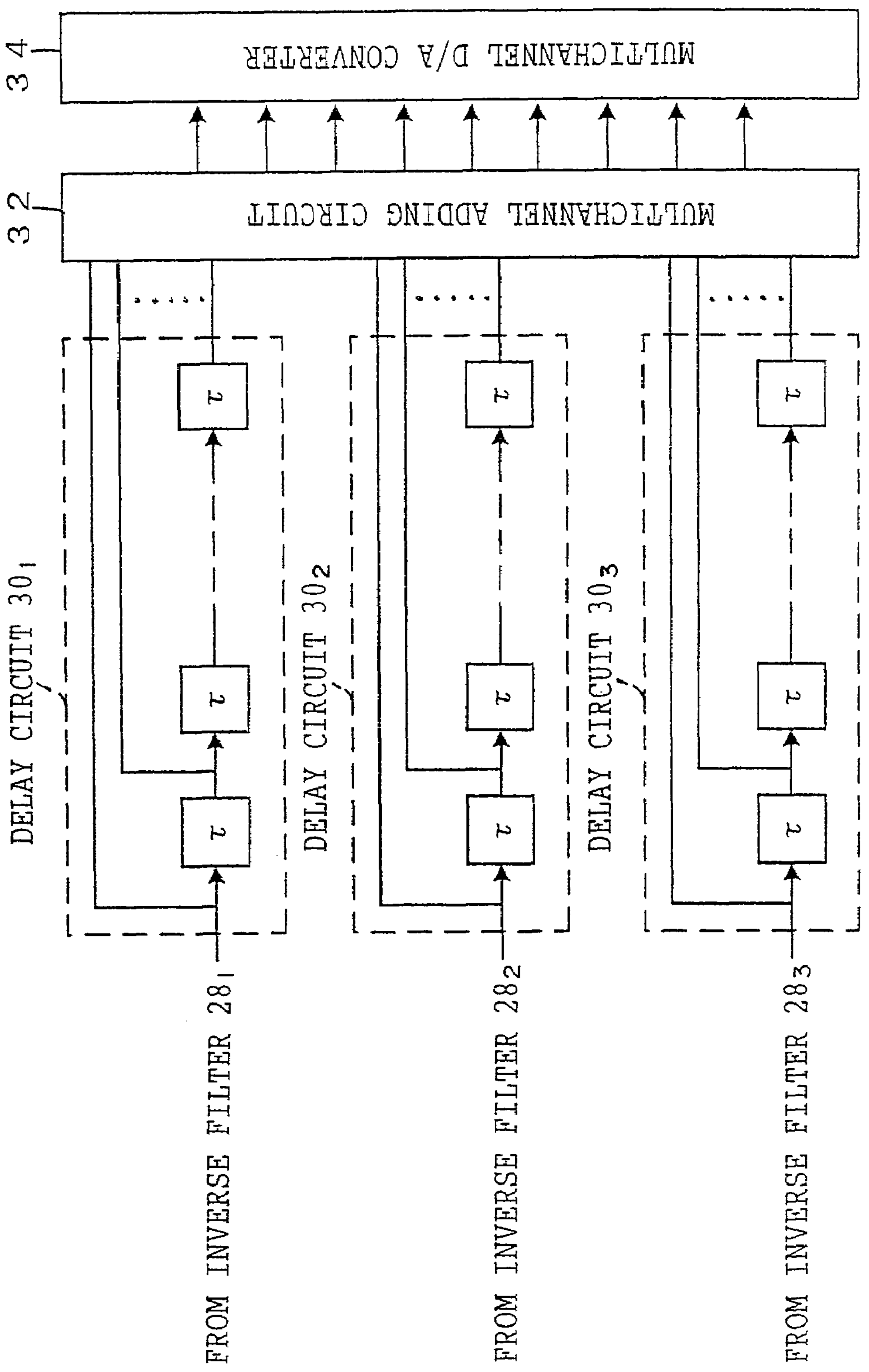
FIG. 8 is a block diagram showing the circuit configuration of delay circuits.

As shown in FIG. 8, the delay circuits $\mathbf{30}_1$ to $\mathbf{30}_3$ are configured by plural unit delay elements connected in a series. The numbers of these unit delay elements are configured to be one less than the sample number (here, nine) of the digital signals. Also, the sample number of the delay signals is determined in consideration of the problem of the separation of adjacent linear array of flat loudspeakers.

Output terminals of the delay circuits $\mathbf{30}_1$ to $\mathbf{30}_3$ are connected to the multichannel adding circuit 32, and the delay signals obtained by the delay circuits $\mathbf{30}_1$ to $\mathbf{30}_3$ are inputted to the multichannel adding circuit 32. In this example, signals delayed by 0, τ, 2τ, 3τ, 4τ, 5τ, 6τ, 7τ and 8τ (where τ represents the delay times of the unit delay elements) are inputted from the delay circuits to the multichannel adding circuit 32. It should be noted that the delay times of the unit delay elements may differ per unit delay element and may be optional values.

The delayed signals are inputted to the multichannel adding circuit 32 and added to each flat speaker. In a case where $D_1$ represents the delay time resulting from the delay circuit $\mathbf{30}_1$, $D_2$ represents the delay time resulting from the delay circuit $\mathbf{30}_2$ and $D_3$ represents the delay time resulting from the delay circuit $\mathbf{30}_3$, the signal of the delay time $D_1$, the signal of the delay time $D_2$ and the signal of the delay time $D_3$ are digitally added with respect to each of the nine linear array of flat loudspeakers of a speaker array 40. This adding is done so that all of the digital signals that are to be inputted to the linear array of flat loudspeakers positioned at positions corresponding to each linear array of loud speakers are added and outputted from the linear array of flat loudspeakers. By adding the digital signals in this manner, sound waves propagating in the three directions shown in FIGS. 11A to 11C can be outputted from the speaker arrays.

The delay times $D_1$ to $D_3$ can be combined as shown in Table 1. In this example, the signal of the delay time τ from the delay circuit $\mathbf{30}_1$, the signal of the delay time 0 from the delay circuit $\mathbf{30}_2$ and the signal of the delay time 7τ from the delay circuit $\mathbf{30}_3$ are added in correspondence to the flat speaker 2. The signals added to each flat speaker in this manner are inputted to the multichannel D/A converter 34, D/A converted and outputted to the speaker unit 14.

TABLE 1

| | Delay Time $D_1$ | Delay Time $D_2$ | Delay Time $D_3$ |
|---|---|---|---|
| Speaker 1 | 0 | 0 | 8τ |
| Speaker 2 | 1τ | 0 | 7τ |
| Speaker 3 | 2τ | 0 | 6τ |
| Speaker 4 | 3τ | 0 | 5τ |
| Speaker 5 | 4τ | 0 | 4τ |
| Speaker 6 | 5τ | 0 | 3τ |
| Speaker 7 | 6τ | 0 | 2τ |
| Speaker 8 | 7τ | 0 | 1τ |
| Speaker 9 | 8τ | 0 | 0 |

In addition to the speaker array 40, the speaker unit 14 is also disposed with a power amplifier array 38 in which power amplifiers are arranged in correspondence to the linear array of flat loudspeakers of the speaker array 40. The analog signals added to the linear array of flat loudspeakers by the DSP processor 24 are amplified by the power amplifiers corresponding to the linear array of flat loudspeakers and outputted to the linear array of flat loudspeakers of the speaker array 40. Additionally, the sound waves corresponding to the filtered signals, i.e., the sound waves having an antiphase with respect to the noise are outputted, as the control sound 16, from the linear array of flat loudspeakers configuring the speaker unit 14. Namely, "line sound sources", where sound sources are linearly arranged, are pseudo-realized. The line sound sources emit cylindrical waves and have a strong directivity in the direction orthogonal to the arrangement direction.

(Setting of Filter Factors)

Next, the procedure for setting the filter factors of the digital filters of the DSP processor 24 will be described. Here, a case will be described where the filter factor $W_2$ is set to generate the inverse filter $\mathbf{28}_2$, but the inverse filter $\mathbf{28}_1$ and the inverse filter $\mathbf{28}_3$ can also be generated by the same method.

The noise emitted from the noise source S is picked by the sound source microphone $\mathbf{20}_2$ and inputted to the DSP processor 24 via the preamplifier $\mathbf{22}_2$. The inputted signal is DSP-processed and outputted to the speaker unit 14. Then, antiphase waves of the noise are emitted as the control sound 16 towards the top of the sound barrier 10 from the linear array of flat loudspeakers configuring the speaker unit 14, and the diffracted sound at this time is propagated towards the control point C. The noise emitted from the sound source S and the control sound emitted from the speaker unit 14 are picked up by a microphone disposed at the control point C. The picked-up sound waves are A/D converted and inputted to a computer.

Assuming that W(ω) represents the transfer function of the digital filter, the coefficient of the impulse response of the transfer function W(ω) is set to $\delta(t-\tau_{delay})$. $\tau_{delay}$ is the delay time (ms) resulting from the digital filter and can be set to, for example, 300 ms.

Part of the noise emitted from the noise source S reaches the control point C. This transmission path will be called path A. The transfer function of the path A is A(ω). Also, part of the emitted noise is picked up by the sound source microphone $\mathbf{20}_2$, is emitted from the speaker unit 14 via the DPS processor 24, and reaches the control point C. This transmission path will be called path B. The transfer function of path B is B(ω). The signal sound from path A and the signal sound from path B are simultaneously picked up at the control point C.

Assuming that the transfer function of a path C1 from the noise source S to the sound source microphone $\mathbf{20}_2$ is C1(ω) and the transfer function of a path C2 from the speaker unit 14 to the control point C is C2(ω), the transfer function B(ω) of path B is expressed by the following equation. It should be noted that the product of C1(ω) and C2(ω) is equal to the transfer function C(ω) of path C (paths C1+C2).

$$B(\omega)=C\mathbf{1}(\omega)C\mathbf{2}(\omega)W(\omega)=C(\omega)W(\omega)$$

For example, assuming that the transfer function W(ω) of the digital filter equals 1 here, the transfer function B(ω) of path B and the transfer function C(ω) of path C become equivalent.

The filter factor of the digital filter is computed by an explicit method by the following procedure. This computation is conducted by a computer connected to the digital filter. By explicit method here is meant a method where the impulse response of path A and the impulse response of path B are measured beforehand and the filter factor is computed by numerical calculation.

Figure 9A:
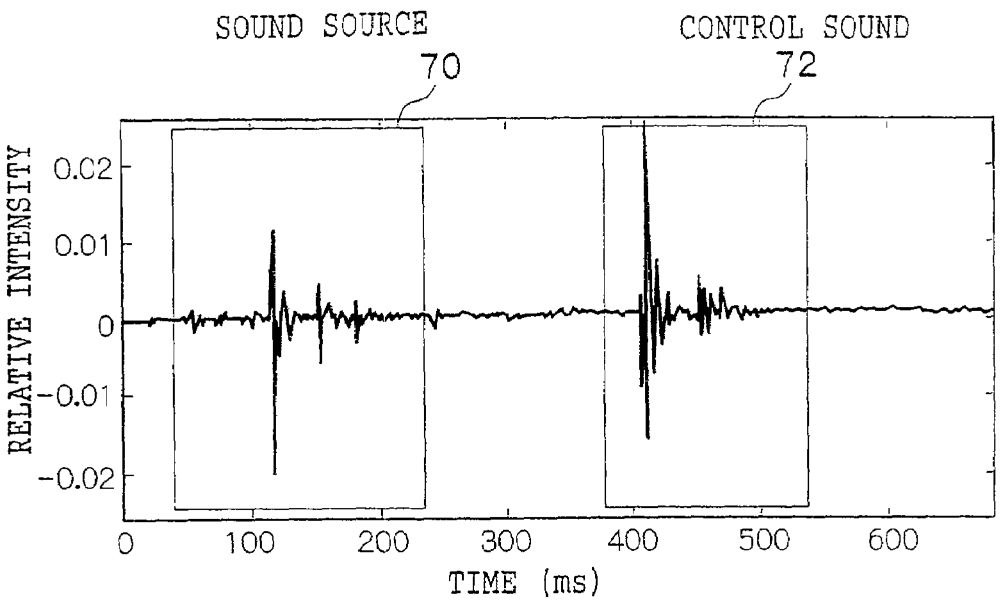
FIGS. 9A and 9B are line diagrams showing impulse responses based on the input of a microphone disposed at the observation point.
Figure 9B:
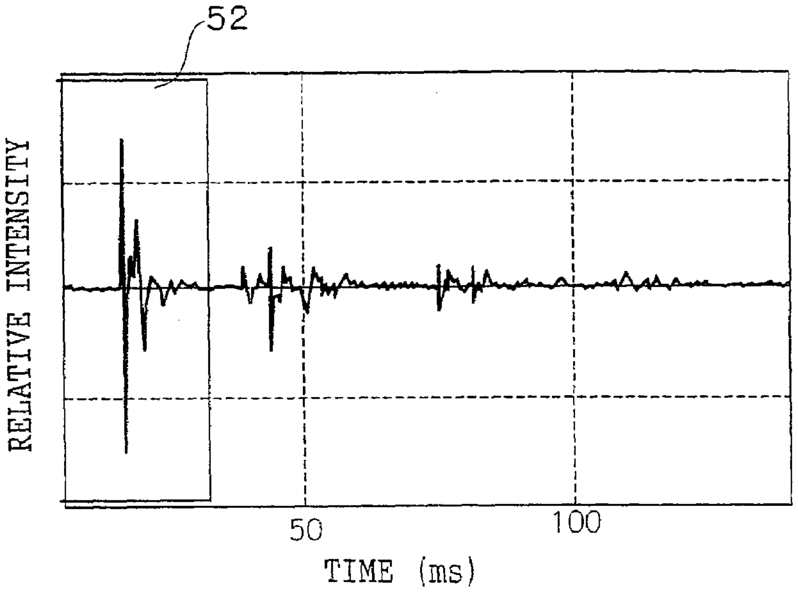

(1) The signal imported to the DSP processor 24 from the microphone disposed at the control point C is converted to an impulse response by an inverse Fourier transform of a cross-correlation function. As shown in FIG. 9A, the impulse response of path C is delayed by $t_{delay}$ (ms) and the impulse responses of path A and path C are temporally divided. Thus, by multiplying this by respective time windows 70 and 72, the impulse responses can be extracted per path. The impulse response of path A is represented by the function a(t) and the impulse response of path C is represented by the function c(t). Moreover, as shown in FIG. 9B, by multiplying a time window 52 by the impulse response a(t) of path A, it is possible to extract only the impulse response of the direct sound.

(2) $c(t-t_{delay})$ in which c(t) is turned back by the amount of the delay time, is made into new c(t). Also, the impulse response of path A, in which the portion corresponding to the direct sound only is extracted, is made into new a(t). Then, the impulse response a(t) of path A is Fourier-transformed to determine the transfer function A(ω) and the impulse response c(t) of path C is Fourier-transformed to determine the transfer function C(ω).

(3) Assuming that the transfer function A(ω) of path A and the transfer function B(ω) of path B satisfy the sound cancellation condition of A(ω)+B(ω)=0, the transfer function W(ω) of the digital filter is expressed by the following equation.

$$W(\omega)=-A(\omega)/C(\omega)$$

Then, W(ω) is computed using the transfer function A(ω) and the transfer function C(ω) obtained by Fourier transformation, and this is inverse-Fourier-transformed to determine the function w(t). The coefficient of this function w(t) is the filter factor $W_2$ of the digital filter. It should be noted that the function w(t) may also be directly determined by a matrix operation from the relation shown in the following equation.

$$w(t)*c(t)-a(t)$$

(where * represents a convolution operation)

The obtained filter factor is set in the digital filter. Thus, the digital filter becomes the inverse filter $\mathbf{28}_2$ that has the transfer function W(ω) and can generate the control sound with the antiphase wave that can cancel the noise.

(Noise Control)

Next, a noise control operation will be described. Noise 12 emitted from the noise source S is picked up by the sound source microphones $\mathbf{20}_1$ to $\mathbf{20}_3$, amplified by the corresponding preamplifiers $\mathbf{22}_1$ to $\mathbf{22}_3$ and inputted to the DSP processor 24. The inverse filters $\mathbf{28}_1$ to $\mathbf{28}_3$ of the DSP processor 24 conduct digital filtering using the digital signals inputted from the A/D converters $\mathbf{26}_1$ to $\mathbf{26}_3$ and the set filter factors $W_1$ to $W_3$.

Figure 10:
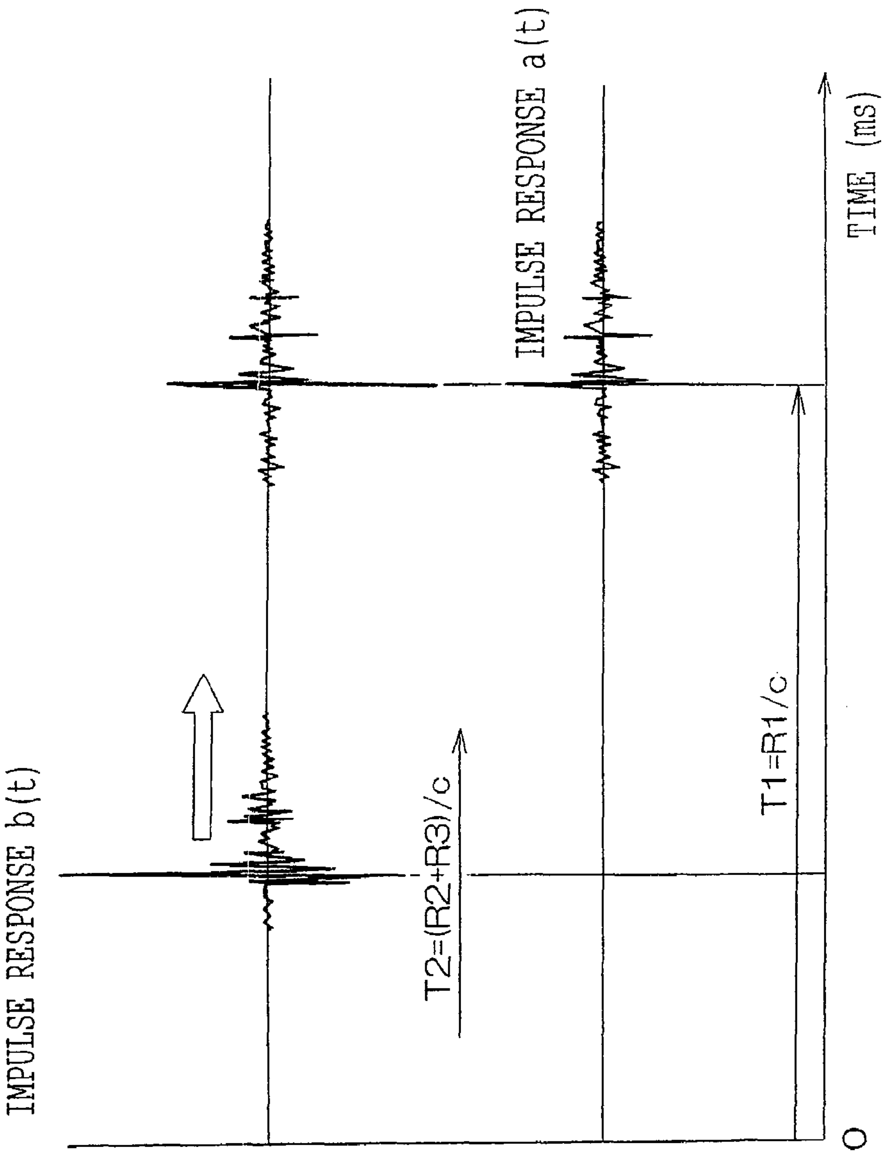
FIG. 10 is an explanatory diagram for describing the action of inverse filters of a DSP processor.

Here, the action of the inverse filters $\mathbf{28}_1$ to $\mathbf{28}_3$ will be described with reference to FIG. 10. The function a(t) represented by the solid line is the impulse response of path A, which is the control target, and the function b(t) represented by the dotted line is the impulse response of path B in a case where it passes through a path circuit not disposed with the inverse filters $\mathbf{28}_1$ to $\mathbf{28}_3$. As will be understood from a comparison of both, by passing through the inverse filters $\mathbf{28}_1$ to $\mathbf{28}_3$, the waveform of the impulse response b(t) is shaped, time-shifted and becomes the same waveform as the control target as represented by the solid line. Thus, a noise reducing effect can be obtained by inverting the phase of the waveform and emitting the wave as the control sound.

The filtered signals are inputted to the delay circuits $\mathbf{30}_1$ to $\mathbf{30}_3$ and delayed in correspondence to the arrangement order of the linear array of flat loudspeakers. The delayed signals are inputted to the multichannel adding circuit 32 and added to each flat speaker. The signals added to each flat speaker are inputted to the multichannel D/A converter 34, D/A converted and outputted to the speaker unit 14. Then, the sound waves corresponding to the filtered signals, i.e., the waves with the antiphase of the noise are emitted as the control sound 16 from the speaker unit 14 towards the control point C, and the noise 12 from the noise source S is canceled at the control point C by the control sound 16.

Figure 11A:
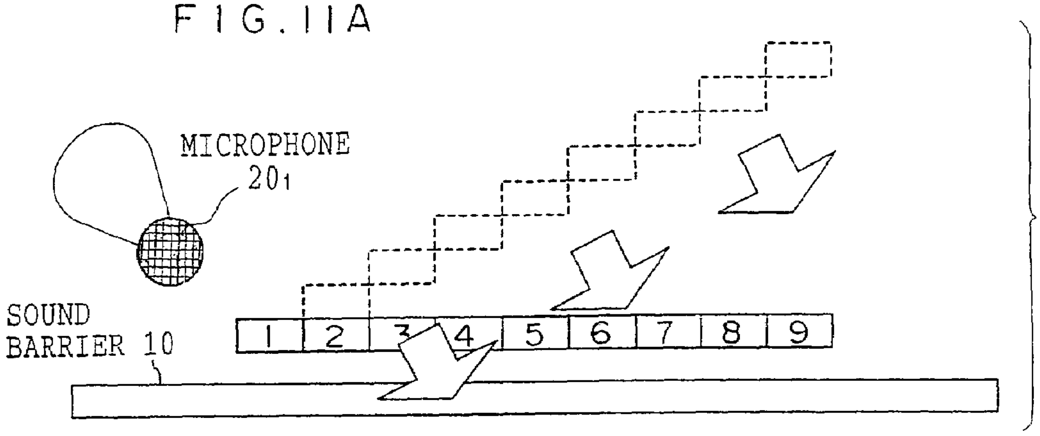
FIGS. 11A to 11C are explanatory diagrams for describing the principle by which a control sound is emitted in two diagonal directions and a front direction from the noise control unit of the first embodiment of the present invention.
Figure 11B:
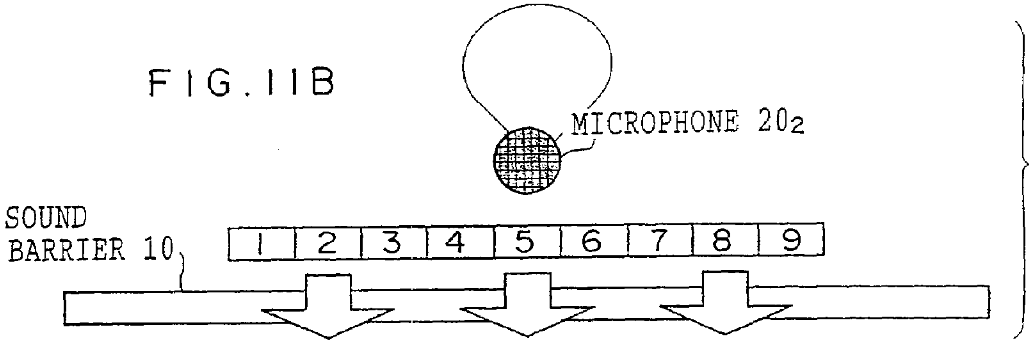
Figure 11C:
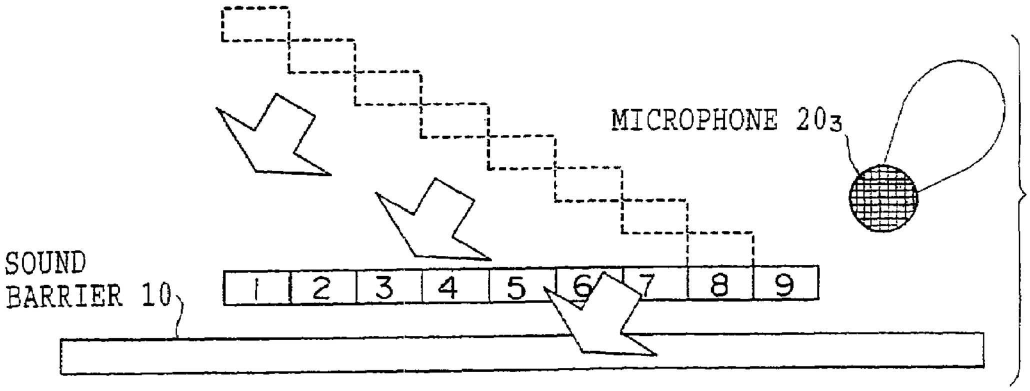

At this time, the control sound 16, which is emitted in the same direction as the noise (front-incident waves) that is made incident at the sound barrier 10 from the front, diffracted at the top and spreads, is diffracted so that the front-incident waves are canceled. Also, the control sound 16, which is emitted in the same direction as the noise (diagonally-incident waves) that is made incident at the sound barrier 10 from diagonal directions, diffracted at the top and spreads, is diffracted so that the diagonally incident waves are canceled. In the present embodiment, as shown in FIGS. 11A to 11C, the control sound 16 is emitted in the front direction and two diagonal directions.

Figure 12:
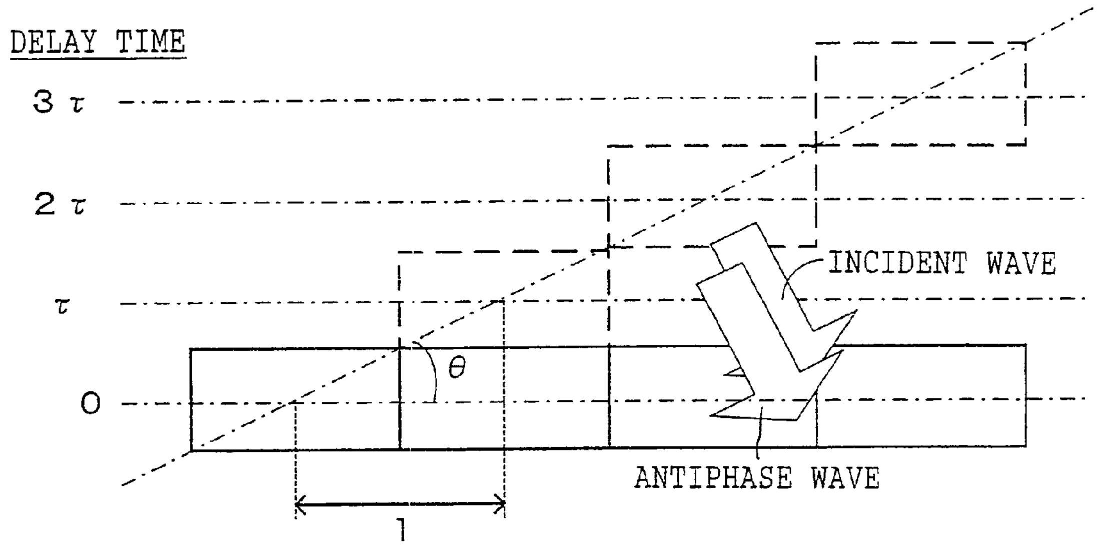
FIG. 12 is an explanatory diagram for describing the relation between a delay time $\tau$ and an inclination $\theta$ of a wavefront of the control sound.

The sound waves picked up by the sound source microphone $20_1$ including a directivity at the incoming side of the automobiles are amplified by the preamplifier and inputted to the DSP processor 24. The signal that is A/D converted by the A/D converter $26_1$ and filtered by the inverse filter $28_1$ is inputted to the delay circuit $30_1$ and delayed in correspondence to the arrangement order of the linear array of flat loudspeakers 1 to 9. Namely, as shown in FIG. 11A, the linear array of flat loudspeakers 1 to 9 are arranged in ascending order from the incoming side of the automobiles (left side of the drawing) towards the outgoing side (right side of the drawing) of the automobiles, and delay times of 0, τ, 2τ, 3τ, 4τ, 5τ, 6τ, 7τ and 8τ are respectively given in the arrangement order to the linear array of flat loudspeakers 1 to 9. By delaying the signal in correspondence to the arrangement order in this manner, the wavefront of the control sound can be slanted in a diagonal direction similar to a case where the linear array of flat loudspeakers 1 to 9 are arranged in one row in a direction forming a predetermined angle with the actual arrangement direction, as represented by the dotted lines. Namely, "line sound sources", where sound sources are linearly arranged, are pseudo realized in the diagonal direction also, A case will now be considered where, as shown in FIG. 12, plural linear array of flat loudspeakers (four in the drawing) are arranged in one row at I m intervals in a predetermined direction, and delay times of 0, τ, 2τ and 3τ are given thereto in the arrangement order. θ represents the angle formed by the wavefront of the noise (incident waves) made diagonally incident with respect to the arrangement direction of the linear array of flat loudspeakers, and c represents sound velocity (m/sec.). In this case, by making τ equal to /sin θ/c (sec.), the wavefront of the control sound (antiphase waves) can be slanted by the angle θ and the diagonally-incident waves can be effectively canceled by the antiphase waves in the same manner as a case where the linear array of flat loudspeakers are arranged in one row in the direction forming the angle θ with the actual arrangement direction.

The sound waves picked up by the microphone $20_2$ including a directivity in the front direction are amplified by the preamplifier and inputted to the DSP processor 24. The signal that is A/D converted by the A/D converter $26_2$ and filtered by the inverse filter $28_2$ is inputted to the delay circuit $30_2$ but is not delayed because the delay time is set to 0. Thus, as shown in FIG. 11B, a control sound having a strong directivity in the direction (front direction) orthogonal to the arrangement direction of the linear array of flat loudspeakers 1 to 9 is emitted.

The sound waves picked up by the microphone $20_3$ including a directivity at the outgoing side of the automobiles are amplified by the preamplifier and inputted to the DSP processor 24. The signal that is A/D converted by the A/D converter $26_3$ and filtered by the inverse filter $28_3$ is inputted to the delay circuit $30_3$ and delayed in correspondence to the arrangement order of the linear array of flat loudspeakers 1 to 9. Namely, as shown in FIG. 11C, the linear array of flat loudspeakers 1 to 9 are arranged in ascending order from the incoming side of the automobiles towards the outgoing side of the automobiles, and delay times of 8τ, 7τ, 6τ, 5τ, 4τ, 3τ, 2τ, 1τ and 0 are respectively given in the arrangement order to the linear array of flat loudspeakers 1 to 9. By delaying the signal in correspondence to the arrangement order in this manner, the wavefront of the control sound can be slanted in a diagonal direction similar to a case where the linear array of flat loudspeakers 1 to 9 are arranged in one row in a direction forming a predetermined angle with the actual arrangement direction, as represented by the dotted lines.

Figure 13:
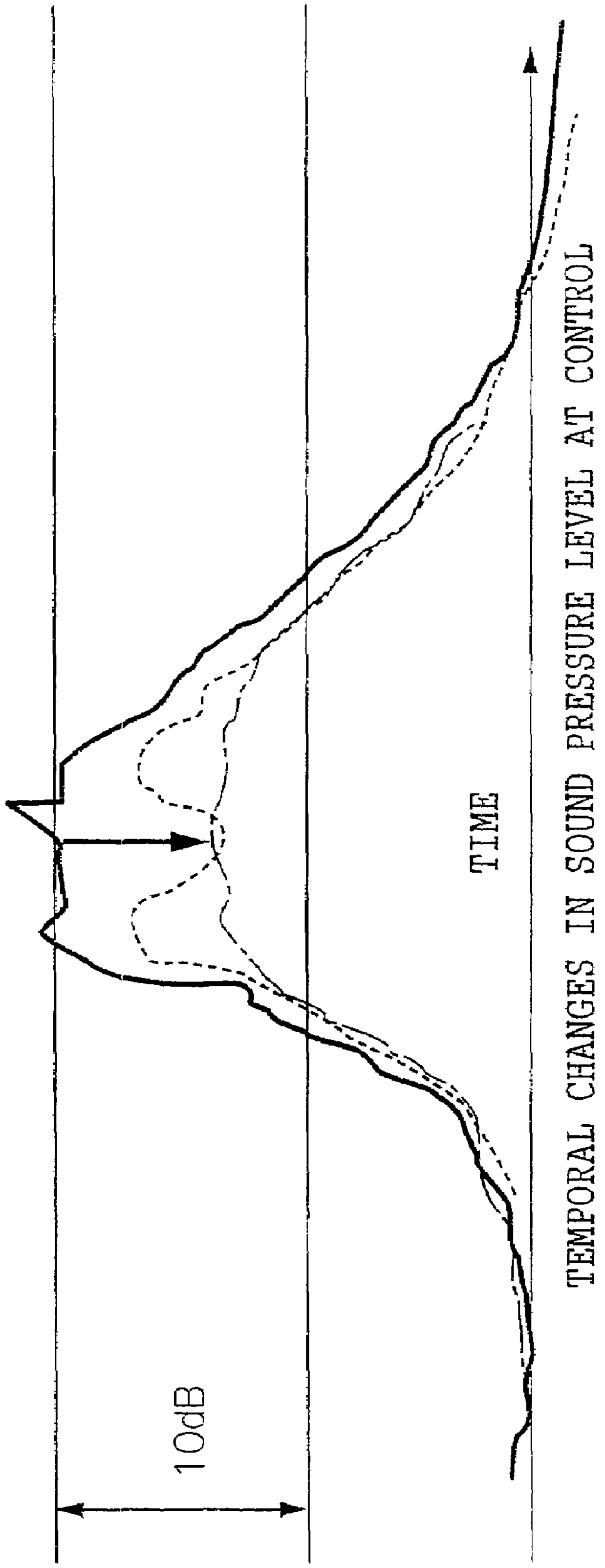
FIG. 13 is a graph showing temporal changes in the sound pressure level at the control point C of the noise propagated from the noise sources S.

FIG. 13 shows temporal changes in the sound pressure level at the control point C of the noise propagated from the noise source S. Because the position of the noise source S changes from point A to point B, point C and point D in correspondence to the travel of the automobile, the sound pressure level at the control point C also changes in correspondence thereto. The solid line represents the sound pressure level in a case where ANC is not conducted. The dotted line represents the sound pressure level in a case where only control of the front-incident waves is conducted, and the single-dot chain line represents the sound pressure level in a case where control of the front-incident waves and control of the diagonally-incident waves are conducted simultaneously. As will be understood from the drawing, in the case where only control of the front-incident waves is conducted, the sound pressure level drops only when the noise source S is present at point C in front of the control point C, but the sound pressure level drops overall regardless of the positions of the noise source S in the case where control of the front-incident waves and control of the diagonally-incident waves are conducted simultaneously.

Figure 14A:
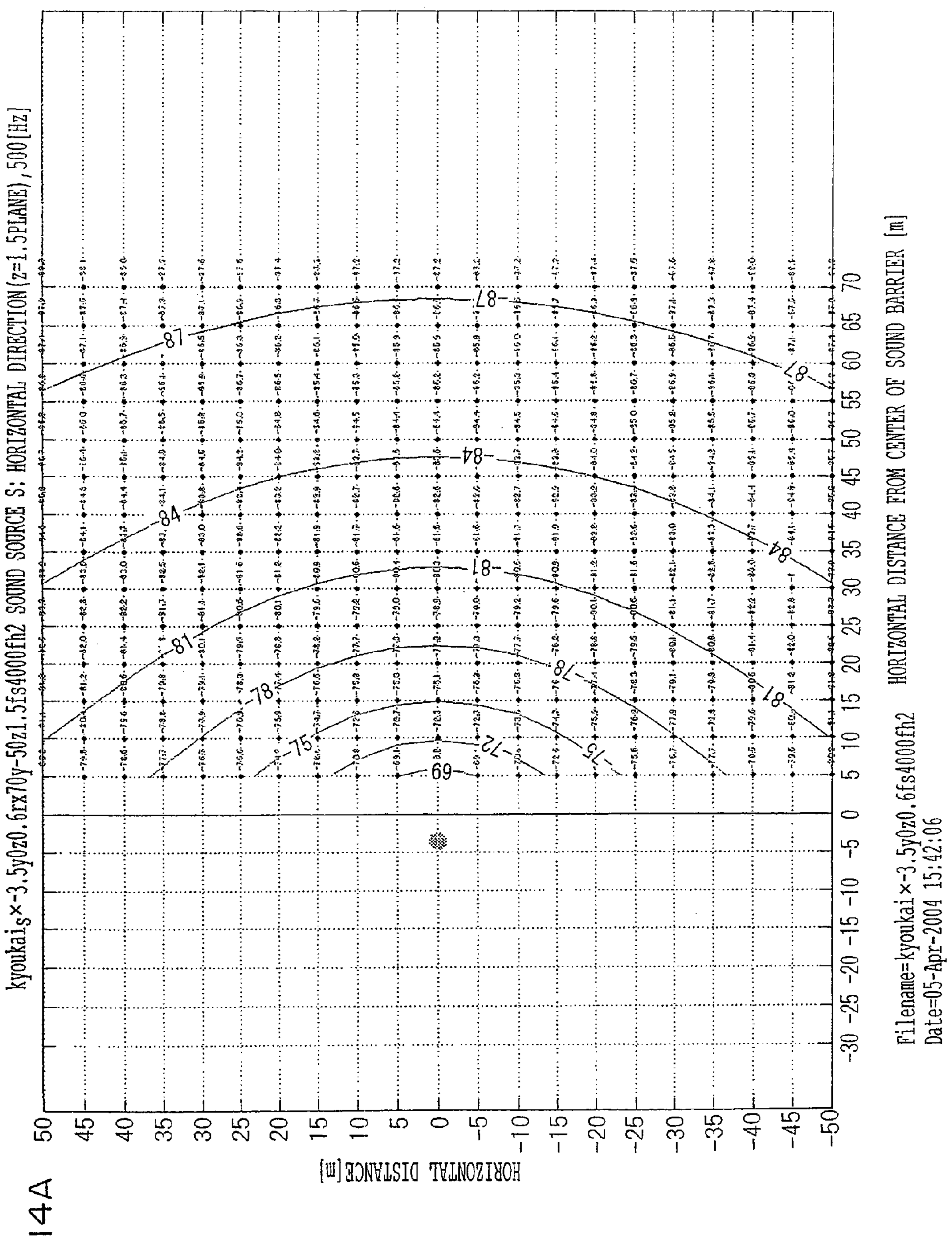
FIG. 14A is a line diagram showing simulation results of the changes in sound pressure level in the vicinity of the noise control unit of the first embodiment of the present invention.

Further, FIG. 14A shows simulation results of the sound pressure level distribution in the vicinity of the sound barrier 10. The simulation was conducted at a road provided with 2 m-high sound barriers set 3.5 m from the road, where the sound sources were positioned 0.5 m above the road surface and set at a power level of 0 dB, and sound-receiving points were positioned at a height of 1.5 m from the ground surface at the outer sides of the sound barriers. The asymptotic equation of Brown & Senior was used with the condition that there was no thickness at the non-directional point sound sources (Takao Kawai, dissertation (1979)). As will be understood from the results, sound is carried not only in a frontal direction at the outer sides of the sound barriers, but also in a diagonal direction.

Figure 14B:
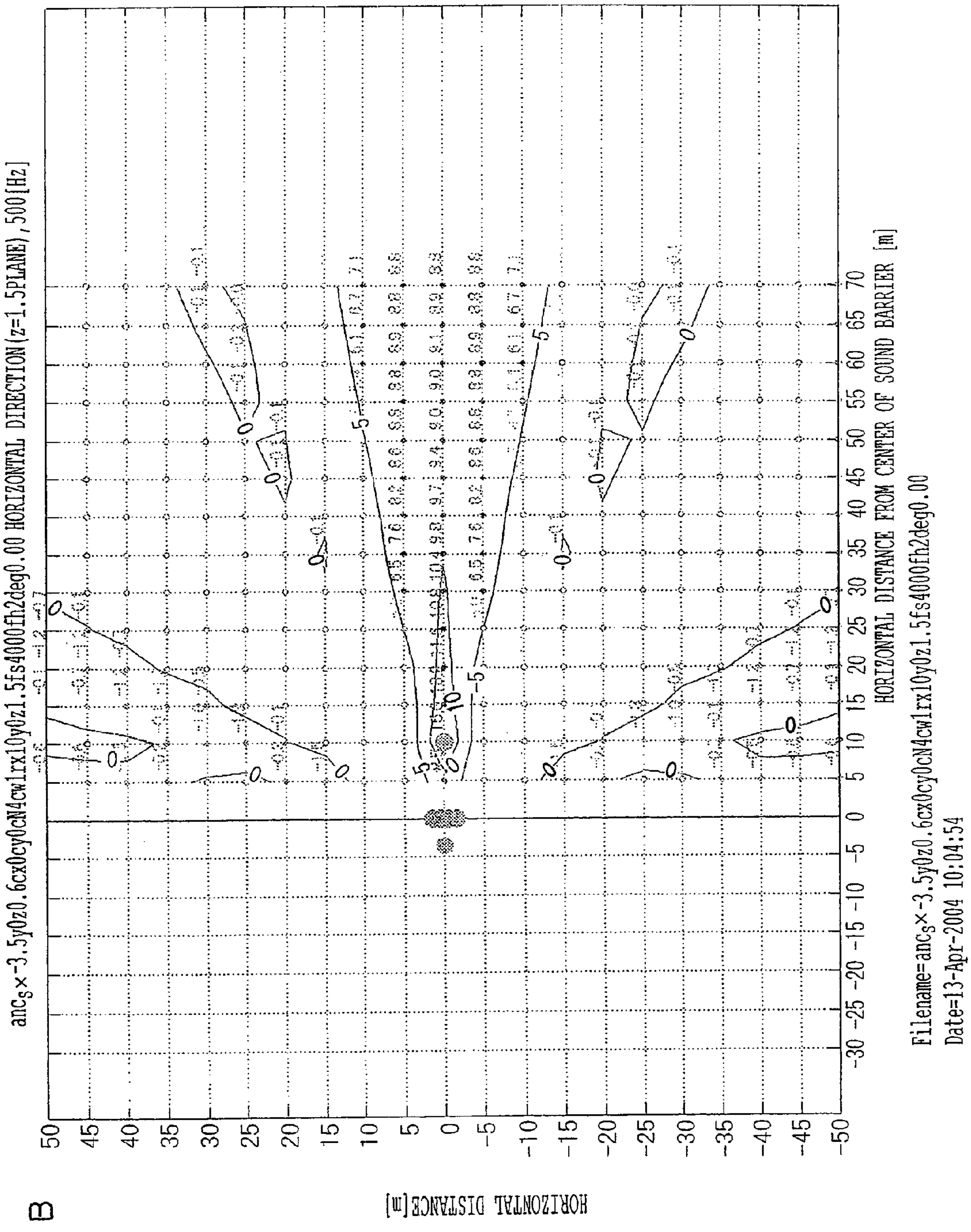
FIG. 14B is a line diagram showing the noise reduction simulation results when control is performed in a frontal direction only in the first embodiment of the present invention.

FIG. 14B illustrates the simulation results of the amount of noise reduction achieved when control is performed only in a frontal direction. In contrast with the sound pressure level simulation results in FIG. 14A, the results of the noise reduction simulation shown in FIG. 14B are the sound pressure level simulation results achieved when control is performed in a frontal direction only.

Figure 14C:
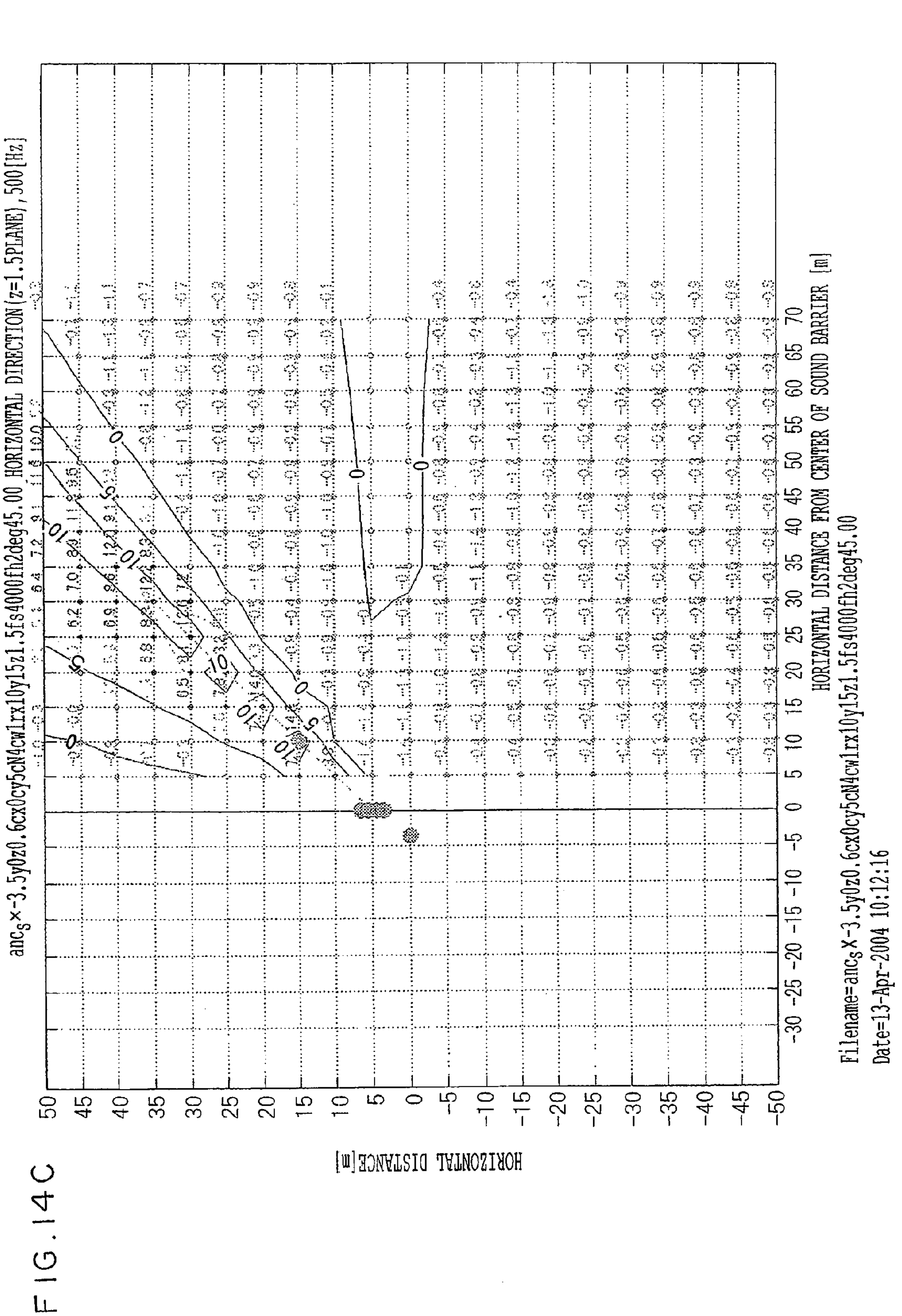
FIG. 14C is a line diagram showing the noise reduction simulation results when control is performed in a diagonal direction only with the control sound slanted in a diagonal direction in the first embodiment of the present invention.

FIG. 14C shows the simulation results of the amount of noise reduction achieved when the wavefront of the control sound is slanted in a diagonal direction and control is performed only in the diagonal direction. In contrast with the sound pressure level simulation results shown in FIG. 14A, the noise reduction simulation results shown in FIG. 14C are the sound pressure level simulation results achieved when control is performed in a diagonal direction only. As is evident from these results, control of diagonal sound can be efficiently carried out by performing control in a diagonal direction.

As described above, in the present embodiment, the noise control units are added to the sound barriers on an expressway. The noise control units are disposed with plural sound source microphones having a strong directivity in mutually different directions and generate a control sound in correspondence to the incident directions of the noise, whereby the noise control units control front-incident waves and diagonally-incident waves and can effectively reduce noise propagating from various directions due to the travel of automobiles that are moving sound sources.

It should be noted that, although an example was described where digital signals were converted to analog signals after the digital signals were added by the multichannel adding circuit, the invention may also be configured so that the output of the inverse filters is plurally divided, converted to analog signals, and the analog signals are added using a multichannel analog adding circuit and inputted to linear array of loudspeakers.

SECOND EMBODIMENT

A traffic noise reducing system pertaining to a second embodiment has the same configuration as that of the first embodiment, except that the noise control units of the second embodiment are configured to include a single sound source microphone and plural speaker units. Therefore, description of identical portions will be omitted and only the points of difference will be described.

Figure 15:
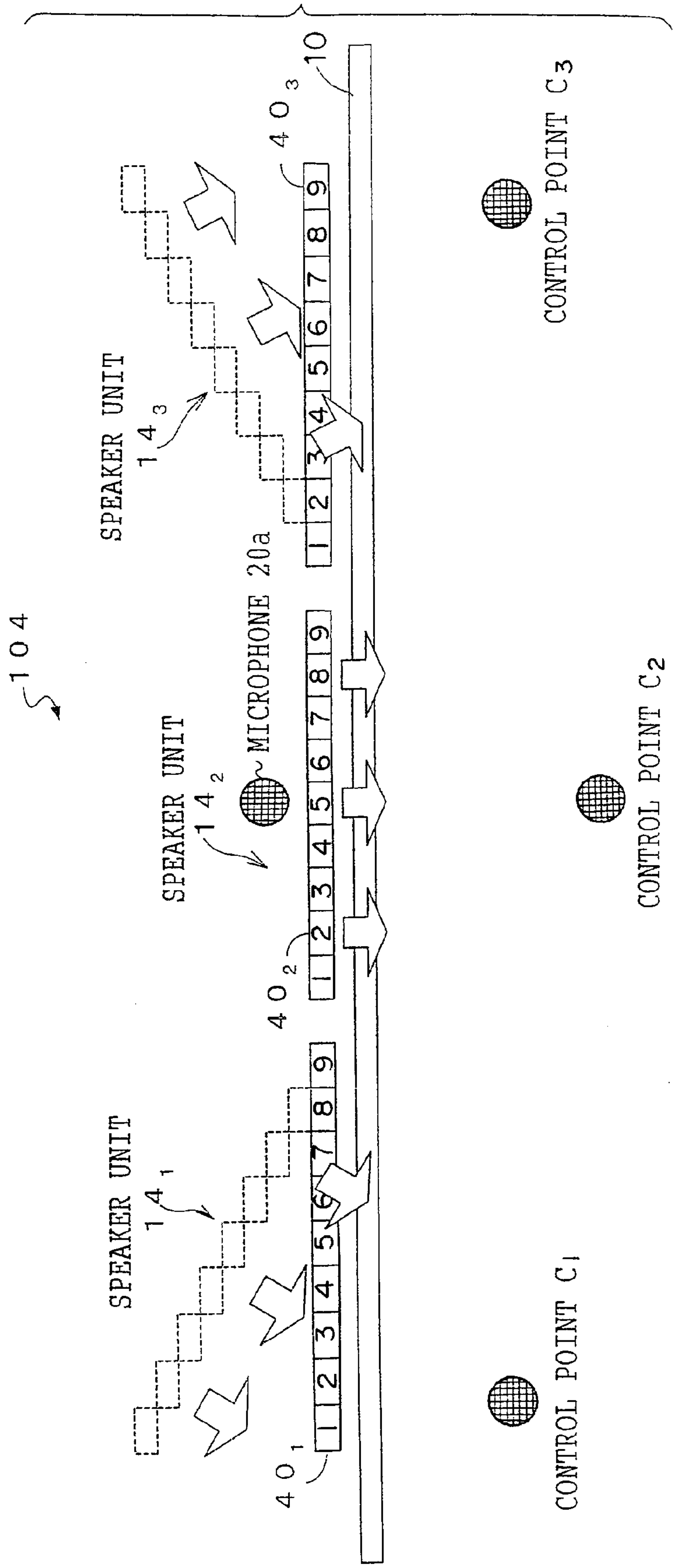
FIG. 15 is a plan diagram showing the schematic configuration of a noise control unit of a second embodiment of the present invention.

The noise control units of the present embodiment are plurally disposed along sound barriers. Because the configurations of the noise control units are the same, one noise control unit will be described. As shown in FIG. 15, a noise control unit 104 is disposed at the sound source side of the sound barrier 10 and includes plural (three in the drawing) speaker units $\mathbf{14}_1$ to $\mathbf{14}_3$ and a single sound source microphone 20*a*.

The speaker units $\mathbf{14}_1$ to $\mathbf{14}_3$ are arranged at predetermined intervals along the sound barrier 10 and respectively include speaker arrays $\mathbf{40}_1$ to $\mathbf{40}_3$ in which plural (nine in the drawing) linear array of flat loudspeakers are arranged in one row along the sound barrier 10. It should be noted that the length of each speaker unit in the speaker arrangement direction can be, for example, about 5 m. Thus, the length of the noise control unit 104 in the speaker arrangement direction is about 15 m.

The sound source microphone 20*a* is disposed in front of the central speaker unit $\mathbf{14}_2$ and has a strong directivity in the incident directions (in the drawing, three directions including two diagonal directions at the incoming side and the outgoing side and the front direction) of the noise waves that are the control target Similar to the first embodiment, the speaker units $\mathbf{14}_1$ and $\mathbf{14}_3$ are disposed at the inner side of the sound barrier 10 at a predetermined distance away from the upper edge of the sound barrier 10 so that the control sound 16 is diffracted at the top of the sound barrier 10. Also, the speaker units $\mathbf{14}_1$ to $\mathbf{14}_3$ emit the control sound 16 towards the top of the sound barrier 10 so that the control sound 16 diffracted at the top of the sound barrier 10 reaches control points $C_1$ to $C_3$ that are set at the outer side of the sound barrier 10 and in correspondence to the speaker units.

Figure 16:
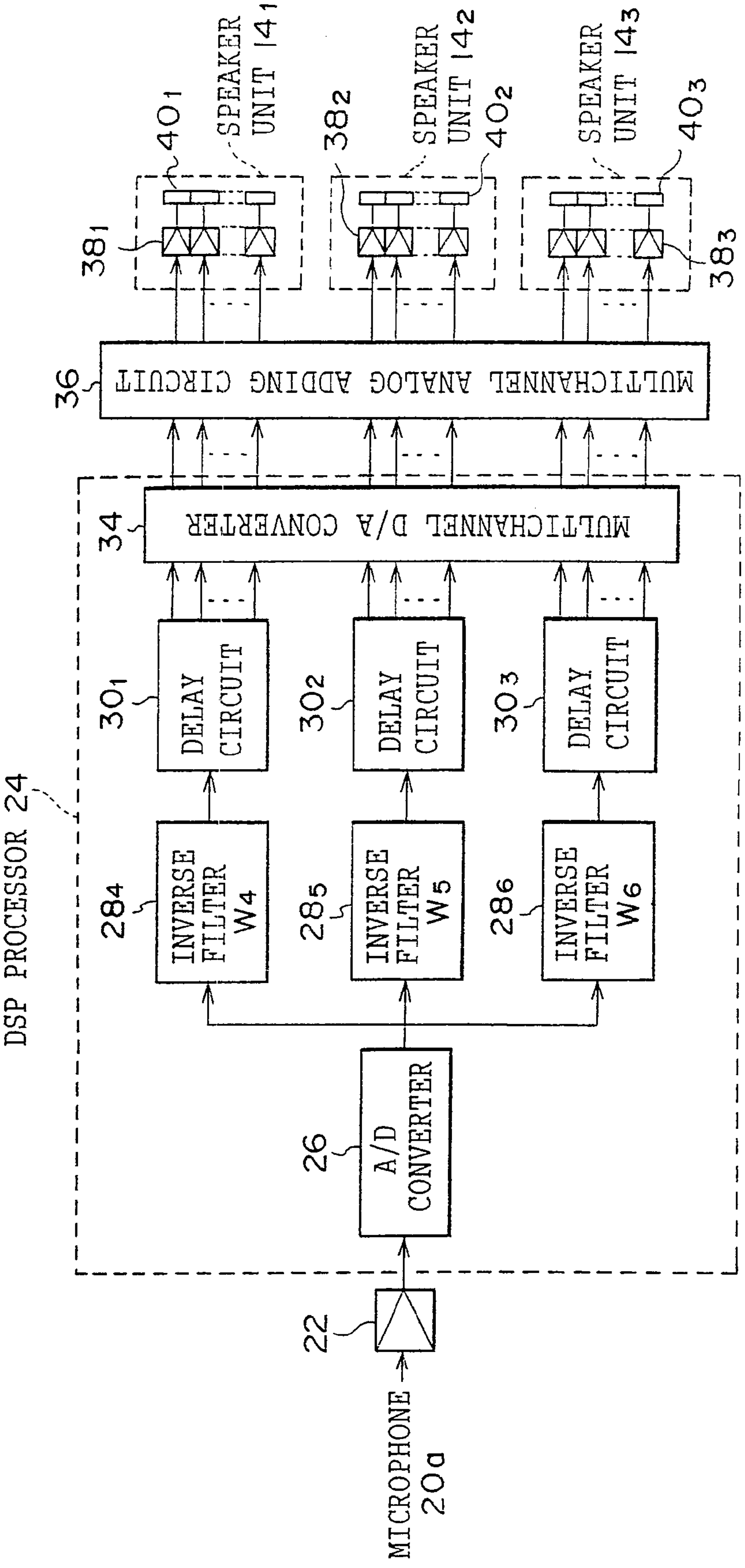
FIG. 16 is a block diagram showing the schematic configuration of the noise control unit of the second embodiment of the present invention.

Also, the DSP processor 24 of the noise control unit 104 is connected to the sound source microphone 20*a* via a preamplifier 22 and is connected to each of the speaker units $\mathbf{14}_1$ to $\mathbf{14}_3$. In the present embodiment, a multichannel analog adding circuit 36 that adds analog signals is connected between the multichannel D/A conversion circuit 34 and the speaker u nits as shown in FIG. 16. The multichannel analog adding circuits of adjacent noise control units are mutually connected. It should be noted that the multichannel analog adding circuits may be disposed inside the speaker units, interconnected in noise control unit units, and the multichannel analog adding circuits of adjacent noise control units may be interconnected. The sound waves picked by the sound source microphone 20*a* are amplified by the corresponding preamplifier 22 and inputted to the DSP processor 24.

As shown in FIG. 16, the )DSP processor 24 is disposed with an A/D converter 26, inverse filters $\mathbf{28}_4$ to $\mathbf{28}_6$ whose filter factors are predetermined, delay circuits $\mathbf{30}_1$ to $\mathbf{30}_3$ that delay the signals in correspondence to the arrangement order of the linear an ay of flat loudspeakers, and the multichannel D/A converter 34. The inverse filters, the delay circuits and the speaker units are all disposed in the same number. The setting of the filter factors $W_4$, $W_5$ and $W_6$ is conducted in the same manner as was previously described.

The inverse filters $\mathbf{28}_4$ to $\mathbf{28}_6$ conduct digital filtering using the digital signal inputted from the A/D converter 26 and the set filter factors. The filtered signals are inputted to the delay circuits $\mathbf{30}_1$ to $\mathbf{30}_3$ and delayed in correspondence to the arrangement order of the linear array of flat loudspeakers. The delay signals obtained by the delay circuits $\mathbf{30}_1$ to $\mathbf{30}_3$ are inputted to the multichannel D/A converter 34, D/A converted, added by the multichannel analog adding circuit 36 and outputted to the corresponding speaker units $\mathbf{14}_1$ to $\mathbf{14}_3$. At this time, the multichannel analog adding circuit 36 adds the analog signals to be inputted to each of the linear array of flat loudspeakers positioned at corresponding positions of the speaker arrays, adds the analog signals to be inputted to adjacent noise control units as needed, and outputs these from the linear array of loudspeakers. Thus, the noise can be effectively reduced because the direction of the sound waves emitted from the speaker units changes in accompaniment with the movement of the noise.

In the present embodiment, delay times of, for example, 8τ, 7τ, 6τ, 5τ, 4τ, 3τ, 2τ, 1τ and 0 are given in the arrangement order and in correspondence to the linear array of flat loudspeakers 1 to 9 to the signal outputted to the speaker unit $\mathbf{14}_1$ disposed at the incoming side of the automobiles. Also, delay times of, for example, 0, τ, 2τ, 3τ, 4τ, 5τ, 6τ, 7τ and 8τ are given in the arrangement order and in correspondence to the linear array of flat loudspeakers 1 to 9 to the signal outputted to the speaker unit $\mathbf{14}_3$ disposed at the outgoing side of the automobiles. By delaying the signals in this manner in correspondence to the arrangement order of the linear array of flat loudspeakers, the wavefront of the control sound can be slanted in a diagonal direction similar to a case where the linear array of flat loudspeakers 1 to 9 are arranged in one row in a direction forming a predetermined angle with the actual arrangement direction, as represented by the dotted lines in FIG. 15, and the diagonally-incident waves can be effectively canceled by antiphase waves.

It should be noted that the signal outputted from the central speaker unit $\mathbf{14}_2$ is not delayed. Thus, a control sound having a strong directivity in the direction (front direction) orthogonal to the arrangement direction of the linear array of flat loudspeakers 1 to 9 is emitted from the speaker unit $\mathbf{14}_2$.

In addition to the corresponding speaker arrays $\mathbf{40}_1$ to $\mathbf{403}_1$ the speaker units $\mathbf{14}_1$ to $\mathbf{14}_3$ are also disposed with power amplifier arrays $\mathbf{38}_1$ to $\mathbf{38}_3$ in which power amplifiers are arranged in correspondence to the linear array of flat loudspeakers of the speaker arrays $\mathbf{40}_1$ to $\mathbf{40}_3$. The analog signals that are processed and D/A converted by the DSP processor 24 per speaker unit are amplified by the power amplifier arrays $\mathbf{38}_1$ to $\mathbf{38}_3$ of the corresponding speaker units $\mathbf{14}_1$ to $\mathbf{14}_3$ and outputted to the flat loudspeakers of the loudspeaker arrays $\mathbf{40}_1$ to $\mathbf{40}_3$.

Additionally, the sound waves corresponding to the filtered signals, i.e., the antiphase waves of the noise are emitted, as the control sound 16, from the speaker units $\mathbf{14}_1$ to $\mathbf{14}_3$ towards the control points $C_1$ to $C_3$, and the noise 12 from the noise source S is canceled by the control sound 16 at the control points $C_1$ to $C_3$.

As described above, in the present embodiment, the noise control units are added to the sound barriers on an expressway. The noise control units are disposed with plural speaker units and generate control sounds in directions that differ per speaker unit in correspondence to the incident directions of the noise, whereby the noise control units control front-incident waves and diagonally-incident waves and can effectively reduce noise propagating from various directions due to the travel of automobiles that are moving sound sources.

Also, because the sound waves picked up by the single sound source microphone are DSP-processed and processing is conducted per speaker unit disposed in correspondence to the incident directions of the noise, the configuration of the DSP processor becomes simple.

THIRD EMBODIMENT

A traffic noise reducing system pertaining to a third embodiment has the same configuration as that of the first embodiment, except that the noise control units of the third embodiment are configured to include a single sound source microphone and plural speaker units. Therefore, description of identical portions will be omitted and only the points of difference will be described.

Figure 17:
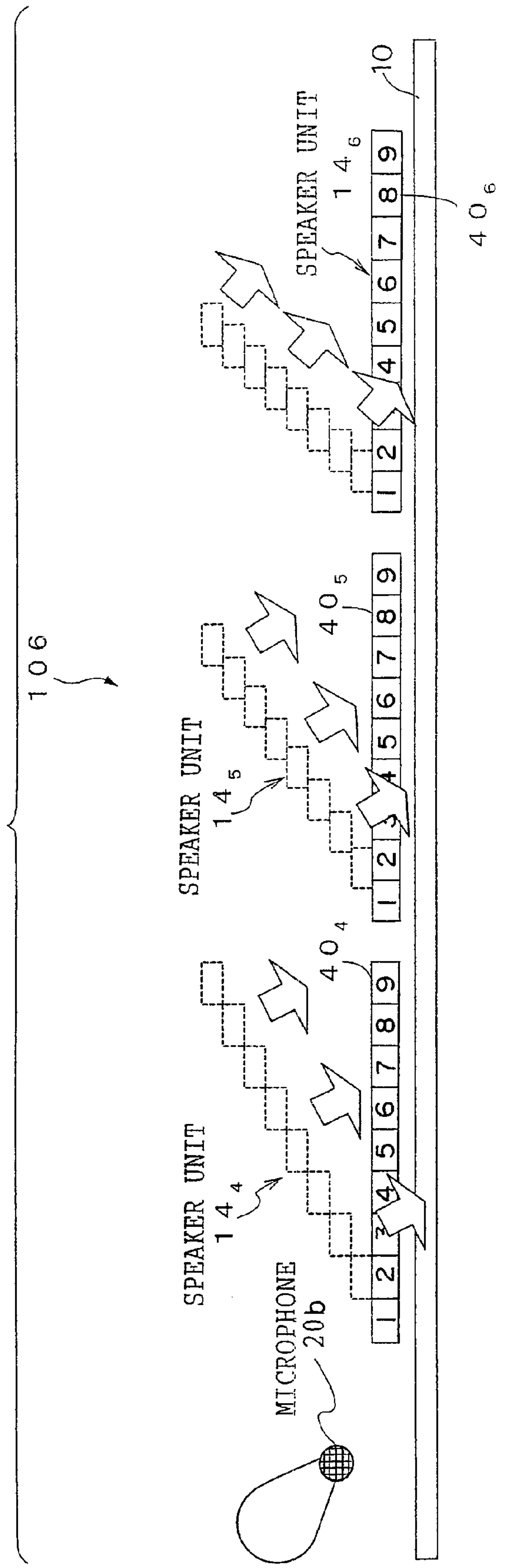
FIG. 17 is a plan diagram showing the schematic configuration of a noise control unit of a third embodiment of the present invention.

As shown in FIG. 17, a noise control unit 106 includes plural (three in the drawing) speaker units $\mathbf{14}_4$ to $\mathbf{14}_6$ and a single sound source microphone 20*b* disposed at the noise source side of the sound barrier 10. The speaker units $\mathbf{14}_4$ to $\mathbf{14}_6$ are arranged at predetermined intervals along the sound barrier 10 and respectively include speaker arrays $\mathbf{40}_4$ to $\mathbf{40}_6$ in which plural (nine in the drawing) linear array of flat loudspeakers are avenged in one row along the sound barrier 10. The sound source microphone 20*b* is disposed at the incoming side of the automobiles with respect to the speaker unit $\mathbf{14}_4$ and has a strong directivity in the incident direction (in the drawing, a diagonal direction at the incoming side of the automobiles) of the noise waves that are the control target.

Similar to the first embodiment, the speaker units $\mathbf{14}_4$ and $\mathbf{14}_6$ are disposed at the inner side of the sound barrier 10 at a predetermined distance away from the upper edge of the sound barrier 10 so that the control sound 16 is diffracted at the top of the sound barrier 10. Also, the speaker units $\mathbf{14}_4$ to $\mathbf{14}_6$ emit the control sound 16 towards the top of the sound barrier 10 so that the control sound 16 diffracted at the top of the sound barrier 10 reaches control points set at the outer side of the sound barrier 10 and in correspondence to the speaker units.

Figure 18:
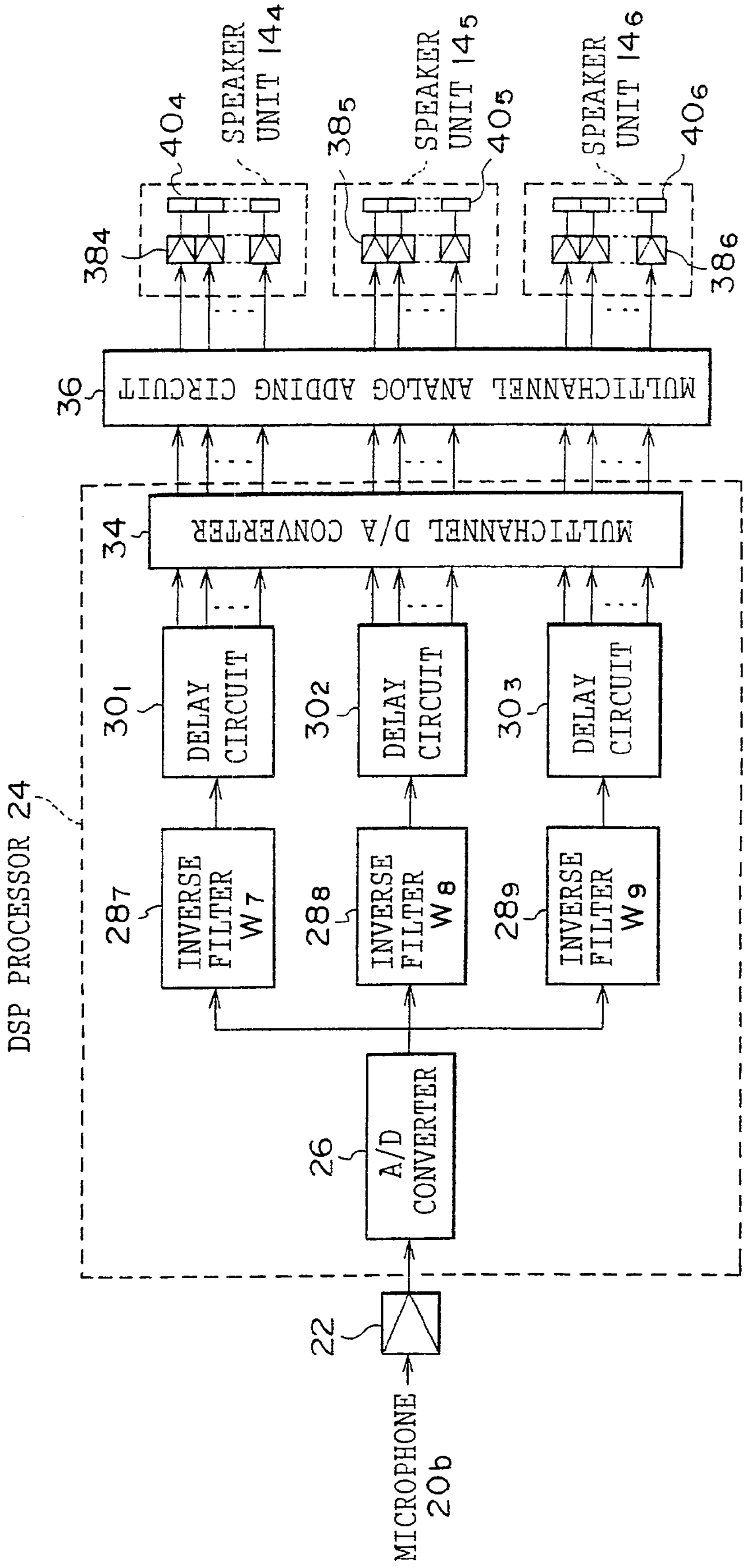
FIG. 18 is a block diagram showing the schematic configuration of the noise control unit of the third embodiment of the present invention.
Figure 19:
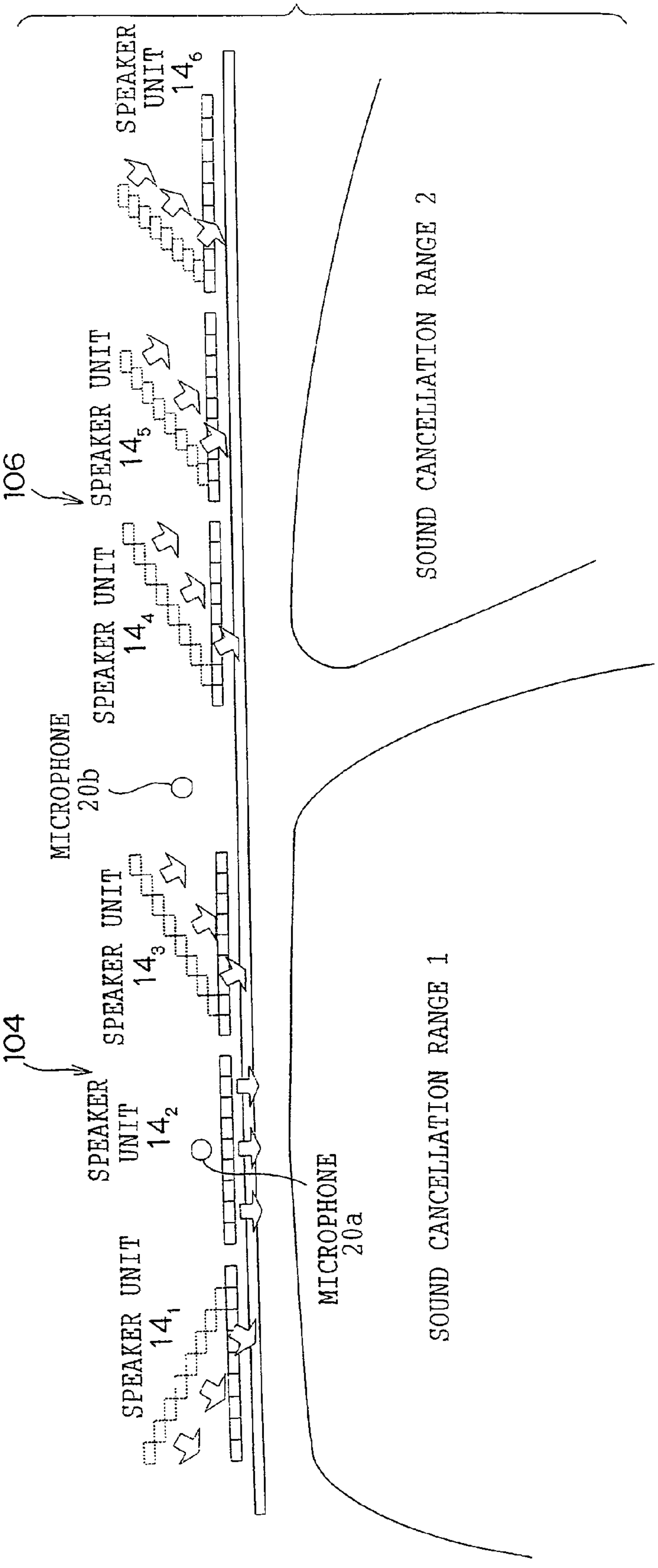
FIG. 19 is a plan diagram showing the schematic configuration of a noise control unit of a fourth embodiment of the present invention

Also, the DSP processor 24 of the noise control unit 106 is connected to the sound source microphone 20*b* via a preamplifier 22 and is connected to each of the speaker units $\mathbf{14}_4$ to $\mathbf{14}_6$ as shown in FIG. 18. The sound waves picked up by the sound source microphone 20*b* are amplified by the corresponding preamplifier 22 and inputted to the DSP.

As shown in FIG. 18, the DSP processor 24 includes an A/D converter 26 disposed in correspondence to the preamplifier 22, inverse filters $\mathbf{28}_7$ to $\mathbf{28}_9$ whose filter factors are preset, the delay circuits $\mathbf{30}_1$ to $\mathbf{30}_3$ that delay the signals in correspondence to the arrangement order of the linear array of flat loudspeakers, and the multichannel D/A converter 34. It should be noted that the setting of the filter factors $W_7$, $W_8$ and $W_9$ is conducted in the same manner as was previously described and that, similar to the second embodiment, the multichannel analog adding circuit 36 is also disposed in the present embodiment.

The inverse filters $\mathbf{28}_7$ to $\mathbf{28}_9$ conduct digital filtering using the digital signal inputted from the A/D converter 26 and the set filter factors. The filtered signals are inputted to the delay circuits $\mathbf{30}_1$ to $\mathbf{30}_3$ and delayed in correspondence to the arrangement order of the linear array of flat loudspeakers. The delay signals obtained by the delay circuits $\mathbf{30}_1$ to $\mathbf{30}_3$ are inputted to the multichannel D/A converter 34, D/A converted, added by the multichannel analog adding circuit 36 and outputted to the corresponding speaker units $\mathbf{14}_4$ to $\mathbf{14}_6$.

In the present embodiment, delay times of, for example, 0τ, τ, 2τ, 3τ, 4τ, 5τ, 6τ, 7τ and 8τ are given in the arrangement order and in correspondence to the linear array of flat loudspeakers 1 to 9 to the signal outputted to the speaker unit $\mathbf{14}_4$ disposed at the incoming side of the automobiles. Also, delay times of, for example, 0, 2τ, 4τ, 6τ, 8τ, 10τ, 12τ, 14τ and 16τ are given in the arrangement order and in correspondence to the linear array of flat loudspeakers 1 to 9 to the signal outputted to the speaker unit $\mathbf{14}_5$ disposed in the center. Moreover, delay times of, for example, 0, 3τ, 6τ, 9τ, 12τ, 15τ, 18τ, 21τ and 24τ are given in the arrangement order and in correspondence to the linear array of flat loudspeakers 1 to 9 to the signal outputted to the speaker unit $\mathbf{14}_6$ disposed at the outgoing side of the automobiles.

By delaying the signals in this manner in correspondence to the arrangement order of the linear array of flat loudspeakers, the wavefront of the control sound can be slanted in a diagonal direction similar to a case where the linear array of flat loudspeakers 1 to 9 are arranged in one row in a direction forming a predetermined angle with the actual arrangement direction, as represented by the dotted lines in FIG. 17, and the diagonally-incident waves can be effectively canceled by antiphase waves.

In addition to the corresponding speaker arrays $\mathbf{40}_4$ to $\mathbf{40}_6$, the speaker units $\mathbf{14}_4$ to $\mathbf{14}_6$ are also disposed with power amplifier arrays $\mathbf{38}_4$ to $\mathbf{38}_6$ in which power amplifiers are arranged in correspondence to the linear array of flat loudspeakers of the speaker arrays $\mathbf{40}_4$ to $\mathbf{40}_6$. The signals that are processed and D/A converted by the DSP processor 24 per speaker unit are added, amplified by the power amplifier arrays $\mathbf{38}_4$ to $\mathbf{38}_6$ of the corresponding speaker units $\mathbf{14}_4$ to $\mathbf{14}_6$ and outputted to the linear array of flat loudspeakers of the speaker arrays $\mathbf{40}_4$ to $\mathbf{40}_6$.

Additionally, the sound waves corresponding to the filtered signals, i.e., the antiphase waves of the noise are emitted, as the control sound 16, from the speaker units $\mathbf{14}_4$ to $\mathbf{14}_6$ towards the corresponding control points, and the noise 12 from the noise source S is canceled by the control sound 16 at the control points.

As described above, in the present embodiment, the noise control units are added to the sound barriers on an expressway. The noise control units awe disposed with plural speaker units and generate control sounds in directions that differ per speaker unit in correspondence to the incident direction of the noise, whereby the noise control units control front-incident waves and diagonally-incident waves and can effectively reduce noise propagating from various directions due to the travel of automobiles that are moving sound sources.

In particular, because the sound source microphone is disposed at the incoming side of the automobiles with respect to the speaker units, diagonally-incident waves coming from a distance, i.e., sound waves producing the Doppler Effect can be absorbed. Additionally, because the control sound is generated based on these sound waves, they can also accommodate the Doppler Effect Also, by gradually increasing, from the incoming side of the automobiles to the outgoing side, the angle at which the wavefront of the control sound is slanted, diagonally-incident waves made incident at various angles can be effectively canceled.

Also, because the sound waves picked up by the single sound source microphone are DSP-processed and processing is conducted per speaker unit disposed in correspondence to the incident direction of the noise, the configuration of the DSP processor becomes simple.

FOURTH EMBODIMENT

A traffic noise reducing system pertaining to a fourth embodiment is configured by a combination of the noise control unit 104 of the second embodiment and the noise control unit 106 of the third embodiment. According to this configuration, the noise within a sound cancellation range 1 positioned in the vicinity of the front of the noise control unit 104 can be controlled and reduced by the noise control unit 104, and the noise within a sound cancellation range 2 positioned in a diagonal direction of the noise control unit 104 can be controlled and reduced by the noise control unit 106.

The noise entering the sound cancellation range 2 produces the Doppler Effect. In the noise control unit 104, because the sound source microphone 20*a* is disposed in front of the center speaker unit, the sound waves picked up by the sound source microphone 20*a* are DSP-processed and the control sound is generated, the noise control unit 104 cannot accommodate the Doppler effect.

On the other hand, in the noise control unit 106, because the sound source microphone 20*b* is disposed at the incoming side of the automobiles with respect to the speaker units, the diagonally-incident waves coming from a distance, i.e., the sound waves producing the Doppler effect are picked up and the control sound is generated on the basis of these sound waves. Thus, the noise control unit 106 can accommodate the Doppler Effect.

As described above, in the present embodiment, the front-incident waves and the diagonally-incident waves are controlled and tie noise propagating from various directions due to the travel of the automobiles that are moving sound sources can be effectively reduced in a wider region.

It should be noted that, although examples were described in the first, second and fourth embodiments where noise made incident from the front direction and diagonal directions was reduced, the, noise control unit may also be configured to reduce noise made incident from the front direction, diagonal directions and diagonally rear directions.

What is claimed is:

1. A noise reducing device comprising: a first microphone disposed at a control point set at an outer side of a sound barrier that reduces noise emitted from a noise source; a second microphone disposed at an inner side of the sound barrier and including a directivity in a predetermined direction so as to pick up the noise that is emitted from the noise source and made incident from a diagonal direction with respect to the sound barrier; computing means that computes, on the basis of the output of the first microphone and the output of the second microphone, a filter factor with an explicit method so that the noise at the control point is reduced; a filter that outputs a control signal digitally filtered on the basis of the filter factor computed by the computing means and the output of the second microphone; a control sound source in which unidirectional linear array of plural loudspeakers are arranged in a predetermined direction and which is disposed so that a control sound configured by sound emitted from the linear array of plural loudspeakers is diffracted at an upper edge of the sound barrier and reaches the control point; and an input circuit that inputs, to the linear array of plural loudspeakers and in correspondence to the arrangement order of the linear array of plural loudspeakers, the control signal and a delay control signal in which the control signal is delayed by predetermined times in correspondence to the direction in which the noise is made incident at the sound barrier.

2. The noise reducing device of claim 1, wherein the control sound source is plurally disposed and the input circuit inputs, per control sound source and in correspondence to the arrangement order of the linear array of plural loudspeakers, the control signal and the delay control signal in which the control signal is delayed by predetermined times in correspondence to the direction in which the noise is made incident at the sound barrier.

3. A noise reducing device comprising: a first microphone disposed at a control point set at an outer side of a sound barrier that reduces noise emitted from a noise source; a second microphone disposed at an inner side of the sound barrier and including a directivity in a predetermined direction so as to pick up the noise that is emitted from the noise source and made incident from a diagonal direction with respect to the sound barrier; a third microphone disposed at an inner side of the sound barrier and including a directivity in a predetermined direction so as to pick up the noise that is emitted from the noise source and made incident from a front direction with respect to the sound barrier, computing means that computes, on the basis of the output of the first microphone and the output of the second microphone, a first filter factor with an explicit method so that the noise at the control point is reduced, and which computes, on the basis of the output of the first microphone and the output of the third microphone, a second fitter factor with an explicit method so that the noise at the control point is reduced; a first filter that outputs a first control signal digitally filtered on the basis of the filter factors computed by the computing means and the output of the second microphone; a second filter that generates a second control signal digitally filtered on the basis of the second filter factor computed by the computing means and the output of the third microphone; a control sound source in which unidirectional linear array of plural loudspeakers are arranged in a predetermined direction and which is disposed so that a control sound configured by sound emitted from the linear array of plural loudspeakers is diffracted at an upper edge of the sound barrier and reaches the control point; and an input circuit that inputs, to the linear array of plural loudspeakers and in correspondence to the arrangement order of the linear array of plural loudspeakers, the first control signal and a first delay control signal in which the first control signal is delayed by predetermined times in correspondence to the direction in which the noise is made incident at the sound barrier, and which inputs the second control signal to the linear array of plural loudspeakers.

4. The noise reducing device of claim 3, wherein the control sound source is plurally disposed and the input circuit inputs, in correspondence to the arrangement order of the linear array of plural loudspeakers, the first control signal and the first delay control signal to the linear an ay of plural loudspeakers configuring a predetermined control sound source, and which inputs the second control signal to the linear array of plural loudspeakers configuring another control sound source.

5. A noise reducing device comprising: a first microphone disposed at a control point set at an outer side of a sound barrier that reduces noise emitted from a noise source; a second microphone disposed at an inner side of the sound barrier and including a directivity in a predetermined direction so as to pick up the noise that is emitted from the noise source and made incident from a first diagonal direction with respect to the sound barrier; a third microphone disposed at an inner side of the sound barrier and including a directivity in a predetermined direction so as to pick up the noise that is emitted from the noise source and made incident from a front direction with respect to the sound barrier; a fourth microphone disposed at an inner side of the sound barrier and including a directivity in a predetermined direction so as to pick up the noise that is emitted from the noise source and made incident at the sound barrier from a second diagonal direction that is different from the first diagonal direction; computing means that computes, on the basis of the output of the first microphone and the output of the second microphone, a first filter factor with an explicit method so that the noise at the control point is reduced, and which computes, on the basis of the output of the first microphone and the output of the third microphone, a second filter factor with an explicit method so that the noise at the control point is reduced, and which computes, on the basis of the output of the first microphone and the output of the fourth microphone, a third filter factor with an explicit method so that the noise at the control point is reduced; a first filter that outputs a first control signal digitally filtered on the basis of the filter factors computed by the computing means and the output of the second microphone; a second filter that generates a second control signal digitally filtered on the basis of the second filter factor computed by the computing means and the output of the third microphone; a third filter that generates a third control signal digitally filtered on the basis of the third filter factor computed by the computing means and the output of the fourth microphone; a control sound source in which plural unidirectional linear array of loudspeakers are arranged in a predetermined direction and which is disposed so that a control sound configured by sound emitted from the linear array of plural loudspeakers is diffracted at an upper edge of the sound barrier and reaches the control point; and an input circuit that inputs, to the linear array of plural loudspeakers and in correspondence to the arrangement order of the linear array of plural loudspeakers, the first control signal and a first delay control signal in which the first control signal is delayed by predetermined times in correspondence to the direction in which the noise is made incident at the sound barrier and the third control signal and a second delay control signal in which the third control signal is delayed by predetermined times in correspondence to the direction in which the noise is made incident at the sound barrier, and which inputs the second control signal to the linear array of plural loudspeakers.

6. The noise reducing device of claim 5, wherein the control sound source is plurally disposed and the input circuit inputs, to the linear array of plural loudspeakers configuring a predetermined control sound source and in correspondence to the arrangement order of the linear array of plural loudspeakers, the first control signal and the first delay control signal delayed by time corresponding to the direction in which the noise is made incident at the sound barrier, and which inputs the second control signal to the linear array of plural loudspeakers configuring another control sound source, and which inputs, to the linear array of plural loudspeakers configuring yet another control sound source and in correspondence to the arrangement order of the linear array of plural loudspeakers, the third control signal and the second delay control signal delayed by times corresponding to the direction in which the noise is made incident at the sound barrier.

* * * * *